United States Patent
Liddle et al.

(10) Patent No.: US 11,767,333 B2
(45) Date of Patent: Sep. 26, 2023

(54) BENZIMIDAMIDES COMPOUNDS COMPRISING AN OXABORININ RING

(71) Applicant: INSTITUT NATIONAL DE LA SANTÉ ET DE LA RECHERCHE MÉDICALE (INSERM), Paris (FR)

(72) Inventors: John Liddle, Brentford Middlesex (GB); Ann Louise Walker, Brentford Middlesex (GB); Gemma Victoria White, Brentford Middlesex (GB); Alexis Denis, Romainville (FR); Nerina Dodic, Villebon-sur-Yvette (FR); Marie-Hélène Fouchet, Paris (FR); Anne Bouillot, Villebon-sur-Yvette (FR)

(73) Assignee: INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 0 days.

(21) Appl. No.: 17/738,097

(22) Filed: May 6, 2022

(65) Prior Publication Data

US 2022/0267357 A1    Aug. 25, 2022

Related U.S. Application Data

(63) Continuation of application No. 16/972,732, filed as application No. PCT/EP2019/064599 on Jun. 5, 2019, now Pat. No. 11,352,372.

(30) Foreign Application Priority Data

Jun. 7, 2018 (GB) ..................... 1809378

(51) Int. Cl.
  *C07F 5/02* (2006.01)
(52) U.S. Cl.
  CPC ................... *C07F 5/025* (2013.01)
(58) Field of Classification Search
  CPC ..................................... C07F 5/025
  See application file for complete search history.

(56) References Cited

U.S. PATENT DOCUMENTS 11,352,372 B2 * 6/2022 Liddle .................. A61K 31/69

FOREIGN PATENT DOCUMENTS

| WO | WO-2006089067 A2 * | 8/2006 | ............ A61K 31/69 |
| WO | WO 2006089067 A2 | 8/2006 | |
| WO | WO 2015112079 A1 | 7/2015 | |
| WO | WO 2015112081 A1 | 7/2015 | |

OTHER PUBLICATIONS

Masurier et al., "Inhibitors of Kallikrein-Related Peptidases: An Overview," Medicinal Research Reviews, Mar. 2018, pp. 655-683, vol. 38, No. 2.
International Search Report and Written Opinion, dated Aug. 13, 2018, regarding International Application No. PCT/EP2019/064599, 10 pages.

* cited by examiner

*Primary Examiner* — Golam M Shameem
(74) *Attorney, Agent, or Firm* — Sheppard Mullin Richter & Hampton LLP

(57) ABSTRACT

The invention relates to 4-(1-hydroxy-3,4-dihydro-1H-benzo[c][1,2]oxaborinin-3-yl)benzimidamide derivatives and their use in treating diseases and conditions of the skin (for example, Netherton syndrome, rosacea, atopic dermatitis, psoriasis and itch) caused by abnormally high levels of protease activity (particularly of serine proteases such as kallikreins). In addition, the invention relates to compositions containing the derivatives and processes for their preparation.

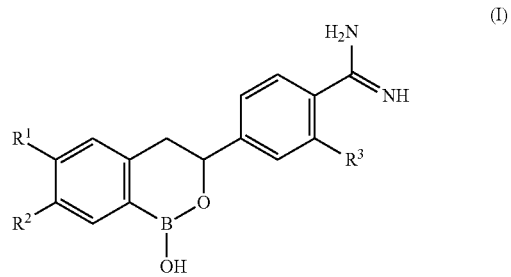

19 Claims, No Drawings

BENZIMIDAMIDES COMPOUNDS COMPRISING AN OXABORININ RING

FIELD OF INVENTION

The invention relates to 4-(1-hydroxy-3,4-dihydro-1H-benzo[c][1,2]oxaborinin-3-yl)benzimidamide derivatives and their use in treating diseases and conditions of the skin (for example, Netherton syndrome, rosacea, atopic dermatitis, psoriasis and itch) caused by abnormally high levels of protease activity (particularly of serine proteases such as kallikreins). In addition, the invention relates to compositions containing the derivatives and processes for their preparation.

BACKGROUND OF THE INVENTION

Netherton syndrome is a genetic skin disease characterised by abnormal desquamation and chronic skin inflammation. The loss of skin barrier function leads to severe dehydration and a high susceptibility to infection. There is a high rate of postnatal mortality, and a general failure to thrive early in life. Patients suffer from a persistent pruritus (itching). Erythroderma is common and ichthyosis often develops. All patients become atopic, manifesting both in the skin and as food allergies.

Netherton syndrome is caused by mutations in the SPINK-5 gene, and is inherited in an autosomal recessive manner. There are over 40 known mutations, but all result in partial or complete loss of expression of the gene product, lympho-epithelial Kazal-type-related inhibitor (LEKTI) in the skin (Chavanas et al, Nature genetics (2000), 25(2), 141-2).

LEKTI is a serine protease inhibitor that is expressed in the most differentiated layer of the epidermis, along with serine proteases such as kallikreins 5, 7 and 14 (KLK-5, -7 and -14). Under normal conditions, LEKTI inhibits protease activity in the lower levels of epidermis, but this inhibition is lost in the more acidic outer layers of the stratum corneum, allowing cleavage of the corneodesmosomes and loss of the outermost layer (desquamation). The absence of LEKTI increases protease activity in the stratum corneum which results in inappropriate cleavage of desmosomal proteins and loss of the entire outer skin layer.

Abnormal protease activity within the epidermis also activates PAR-2 and triggers an inflammatory reaction characterised by increased Th-2 type cytokines such as TSLP. This leads to the observed erythroderma, and the profound pruritus that is characteristic of the disease. The biasing of the immune system towards a TH2 response so early in life also explains the high prevalence of atopy in these patients.

Inhibition of KLK-5 activity in the outer layers of the skin will counteract the partial or complete absence of LEKTI, which drives Netherton Syndrome. This will restore skin barrier function by reducing abnormal desquamation and decrease erythroderma and itching by preventing activation of PAR-2 receptors, decreasing the subsequent inflammatory drive.

Rosacea is an inflammatory skin disease that is estimated to affect 3% of the US population over 30 years of age and is characterized by erythema, papulopustules and telangiectasia. Increased protease activity in the skin has been reported in rosacea (Yamasaki K, et al. Nat. Med. (2007) 13: 975-80). A number of works confirm the pathophysiological role of an increased expression of KLK-5 in rosacea (Two A, et al., J Clin Aesthet Dermatol (2014) 7(1): 20-25). Also, it has been shown that an active ingredient for treating rosacea, such as azelaic acid, has a therapeutic action of inhibiting KLK-5 (Coda A. et al., J Am Acad Dermatol (2013) 69(4): 570-577. These data show the usefulness of inhibitors of the kallikrein protease pathway, and especially of inhibitors of KLK-5 for treating rosacea.

Atopic dermatitis (AD) is a chronic inflammatory skin disease characterised by eczema, pruritus and cutaneous hyperactivity to environmental factors. Clinically unaffected skin in AD manifests impaired skin barrier function favouring microbe and allergen penetration. AD most often starts in childhood before the age of 5 years and approximately 25% of children continue to suffer with the condition through adulthood. Polymorphisms in SPINK-5 have been associated with atopic dermatitis (Walley et al, Nature Genetics 29 (2001)) and accordingly inhibition of the KLK pathway may be effective at treating AD.

Psoriasis is a chronic inflammatory skin disease characterised by disordered keratinocyte proliferation and differentiation, this causes patches of red, flaky, crusty skin covered with silvery scales which may be sore or itchy. The extent of the patches may vary in severity from small and localized to complete body coverage. In psoriatic lesions, T-cell and dendritic cell activation leads abnormal protease activity (Komatsu, N. et al, British Journal of Dermatology (2007) 156(5): 875-883) and accordingly inhibition of the KLK pathway may be effective in treating psoriasis.

In light of the role serine protease enzymes such as KLK-5 play in the cleavage of desmosomal proteins, it is desirable to prepare compounds that inhibit KLK-5 activity, which compounds may be useful in the treatment of diseases and syndromes mediated by the KLK-5 pathway.

BRIEF SUMMARY OF THE INVENTION

According to a first aspect, the invention provides a compound of formula (I) or a pharmaceutically acceptable salt thereof,

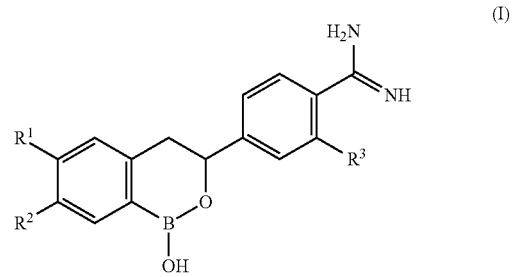

wherein $R^1$, $R^2$ and $R^3$ are defined herein.

Further aspects of the invention include:
i) methods of treating diseases and conditions mediated by the KLK-5 pathway using a compound of formula (I) or a pharmaceutically acceptable salt thereof; exemplary diseases and conditions include, but are not limited to Netherton syndrome, rosacea, atopic dermatitis, psoriasis and itch.
ii) pharmaceutical compositions comprising a) a compound of formula (I) or a pharmaceutically acceptable salt thereof and b) a pharmaceutically acceptable carrier or excipient; and
iii) uses of a compound of formula (I) or a pharmaceutically acceptable salt thereof for treating diseases and conditions mediated by the KLK-5 pathway.

DETAILED DESCRIPTION OF THE INVENTION

According to a first aspect, the invention provides a compound of formula (I) or a pharmaceutically acceptable salt thereof,

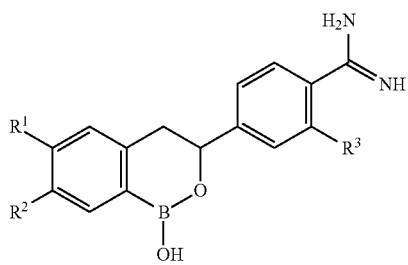
(I)

wherein $R^1$ is H, $R^2$ is $CF_3$ and $R^3$ is 3-pyridylmethoxy, 3-chlorobenzyloxy or H;

$R^1$ is Cl, $R^2$ is F and $R^3$ is 3-pyridylmethoxy; or $R^1$ is H, $R^2$ is H and $R^3$ is 3-pyridylmethoxy.

In an embodiment, the compound of formula (I) is selected from the group consisting of:

4-(1-hydroxy-7-(trifluoromethyl)-3,4-dihydro-1H-benzo[c][1,2]oxaborinin-3-yl)-2-(pyridin-3-ylmethoxy)benzimidamide (Compound 1);

2-((3-chlorobenzyl)oxy)-4-(1-hydroxy-7-(trifluoromethyl)-3,4-dihydro-1H-benzo[c][1,2]oxaborinin-3-yl)benzimidamide (Compound 5);

4-(1-hydroxy-7-(trifluoromethyl)-3,4-dihydro-1H-benzo[c][1,2]oxaborinin-3-yl)benzimidamide (Compound 6);

4-(6-chloro-7-fluoro-1-hydroxy-3,4-dihydro-1H-benzo[c][1,2]oxaborinin-3-yl)-2-(pyridin-3-ylmethoxy)benzimidamide (Compound 7); and 4-(1-hydroxy-3,4-dihydro-1H-benzo[c][1,2]oxaborinin-3-yl)-2-(pyridin-3-ylmethoxy)benzimidamide (Compound 8);

or a pharmaceutically acceptable salt thereof.

In an embodiment, the compound of formula (I) is 4-(1-hydroxy-7-(trifluoromethyl)-3,4-dihydro-1H-benzo[c][1,2]oxaborinin-3-yl)-2-(pyridin-3-ylmethoxy)benzimidamide

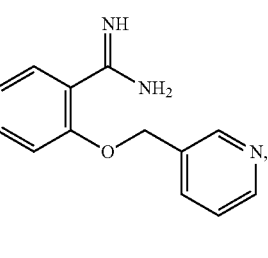

or a pharmaceutically acceptable salt thereof.

In an embodiment, the compound of formula (I) is 2-((3-chlorobenzyl)oxy)-4-(1-hydroxy-7-(trifluoromethyl)-3,4-dihydro-1H-benzo[c][1,2]oxaborinin-3-yl)benzimidamide

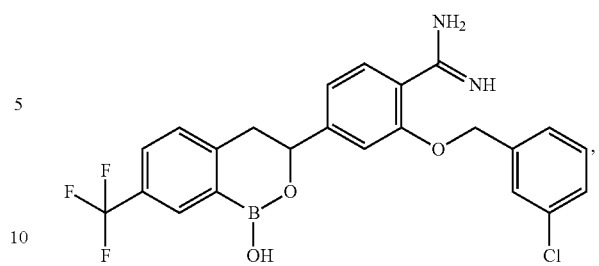

or a pharmaceutically acceptable salt thereof.

In an embodiment, the compound of formula (I) is 4-(1-hydroxy-7-(trifluoromethyl)-3,4-dihydro-1H-benzo[c][1,2]oxaborinin-3-yl)benzimidamide

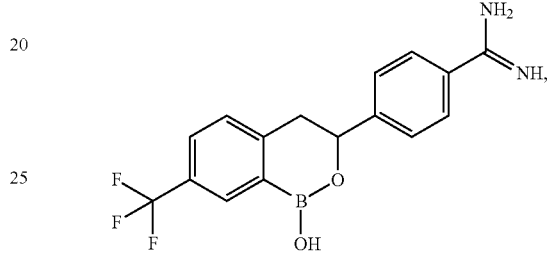

or a pharmaceutically acceptable salt thereof.

In an embodiment, the compound of formula (I) is 4-(6-chloro-7-fluoro-1-hydroxy-3,4-dihydro-1H-benzo[c][1,2]oxaborinin-3-yl)-2-(pyridin-3-ylmethoxy)benzimidamide

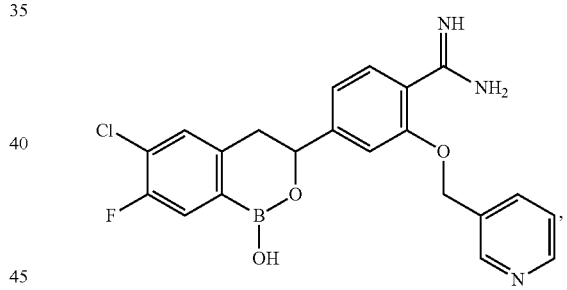

or a pharmaceutically acceptable salt thereof.

In an embodiment, the compound of formula (I) is 4-(1-hydroxy-3,4-dihydro-1H-benzo[c][1,2]oxaborinin-3-yl)-2-(pyridin-3-ylmethoxy)benzimidamide

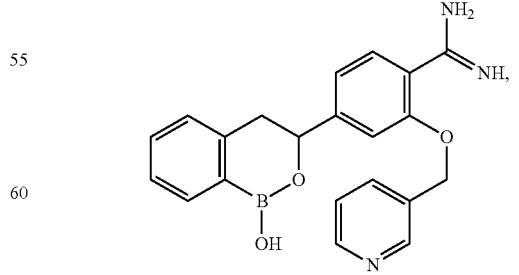

or a pharmaceutically acceptable salt thereof.

The compounds of formula (I) as defined in the first aspect contain a basic centre and may form non-toxic acid addition salts formed with inorganic acids such as hydrochloric, hydrobromic, hydroiodic, sulfuric and phosphoric acid, with carboxylic acids or with organo-sulfonic acids. Examples include 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicylate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate. Pharmaceutically acceptable salts include, amongst others, those described in Berge, J. Pharm. Sci., 1977, 66, 1-19, or those listed in P H Stahl and C G Wermuth, editors, Handbook of Pharmaceutical Salts; Properties, Selection and Use, Second Edition Stahl/Wermuth: Wiley-VCH/VHCA, 2011 (see http://www.wiley.com/WileyCDA/WileyTitle/productCd-3906390519.html).

Salts may be prepared in situ during the final isolation and purification of a compound of formula (I). Alternatively, salts may be prepared by methods known to the art, including treatment with an inorganic or organic acid.

It will be understood that if a compound of formula (I) contains two or more basic moieties, the stoichiometry of salt formation may include 1, 2 or more equivalents of acid. Such salts would contain 1, 2 or more acid counterions, for example, a dihydrochloride salt.

Stoichiometric and non-stoichiometric forms of a pharmaceutically acceptable salt of a compound of formula (I) are included within the scope of the invention, including sub-stoichiometric salts, for example where a counterion contains more than one acidic proton.

It will be appreciated by those skilled in the art that certain protected derivatives of the compounds defined in the first aspect, which may be made prior to a final deprotection stage, may not possess pharmacological activity as such, but may, in certain instances, be administered orally or parenterally and thereafter metabolised in the body to form compounds defined in the first aspect which are pharmacologically active. Such derivatives may therefore be described as "prodrugs". All protected derivatives and prodrugs of compounds defined in the first aspect are included within the scope of the invention. Examples of suitable pro-drugs for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within the compounds defined in the first aspect. Therefore, in a further aspect, the invention provides a prodrug of a compound defined in the first aspect.

The compounds defined in the first aspect, their pharmaceutically acceptable salts or prodrugs, may exist in solvated or hydrated form. Therefore, in a further aspect, the invention provides a solvate or hydrate of a compound defined in the first aspect or a pharmaceutically acceptable salt thereof.

The compounds defined in the first aspect, their pharmaceutically acceptable salts, or solvates or hydrates, may exist in one or more polymorphic form. Therefore, in a further aspect, the invention provides a polymorph of a compound defined in the first aspect or their pharmaceutically acceptable salts, or a polymorph of a solvate or hydrate of a compound defined in the first aspect or a pharmaceutically acceptable salt thereof.

Hereinafter, compounds defined in the first aspect, their salts and prodrugs; any solvates or hydrates of any salt or prodrug; and any polymorph of any compound, salt, solvate or hydrate are referred to as "compounds of the invention". The term "compounds of the invention" also includes all embodiments described for the first aspect.

The compounds of the invention may possess one or more chiral centres and so exist in a number of stereoisomeric forms. All stereoisomers and mixtures thereof are included in the scope of the present invention. Racemic compounds may either be separated using preparative HPLC or preparative SFC and a column with a chiral stationary phase or resolved to yield individual enantiomers utilising methods known to those skilled in the art. In addition, racemic intermediate compounds may be resolved and used to prepare chiral compounds of the invention. In addition, the chiral compounds of the invention may be prepared by chiral synthesis.

In an embodiment, the compound of formula (I) is (R)-4-(1-hydroxy-7-(trifluoromethyl)-3,4-dihydro-1H-benzo[c][1,2]oxaborinin-3-yl)-2-(pyridin-3-ylmethoxy)benzimidamide

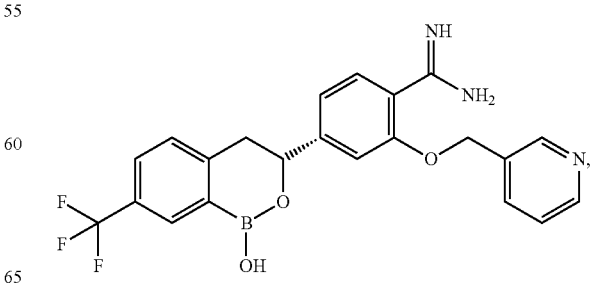

or a pharmaceutically acceptable salt thereof.

In an embodiment, the compound of formula (I) is (S)-4-(1-hydroxy-7-(trifluoromethyl)-3,4-dihydro-1H-benzo[c][1,2]oxaborinin-3-yl)-2-(pyridin-3-ylmethoxy)benzimidamide

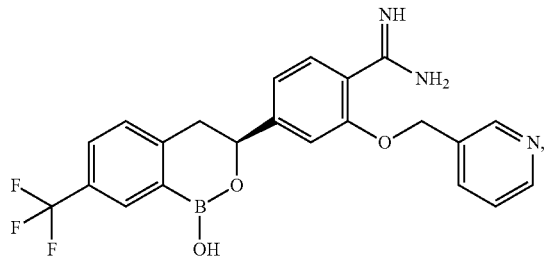 [SMILES: N=C(N)c1ccc([C@@H]2Cc3ccc(C(F)(F)F)cc3B(O)O2)cc1OCc1cccnc1]

or a pharmaceutically acceptable salt thereof.

The compounds of the invention may exist in one or more tautomeric forms. All tautomers and mixtures thereof are included in the scope of the present invention. For example, a claim to 2-hydroxyquinolinyl would also cover its tautomeric form, α-quinolinonyl.

The invention also includes all suitable isotopic variations of a compound of the invention. An isotopic variation of a compound of the invention is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, phosphorus, sulphur, fluorine and chlorine such as $^2H$, $^3H$, $^{11}C$, $^{13}C$, $^{14}C$, $^{15}N$, $^{17}O$, $^{18}O$, $^{35}S$, $^{18}F$ and $^{36}Cl$, respectively. Certain isotopic variations of the invention, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their case of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the compounds of the invention can generally be prepared by conventional procedures such as by the illustrative methods or by the preparations described in the Experimental section hereafter using appropriate isotopic variations of suitable reagents.

Compounds of the invention may be prepared in a variety of ways. In the following reaction schemes and hereafter, unless otherwise stated R$^1$ to R$^3$ are as defined in the first aspect. These processes form further aspects of the invention.

Throughout the specification, general formulae are designated by Roman numerals (I), (II), (III), (IV) etc. Subsets of these general formulae are defined as (Ia), (Ib), (Ic) etc. . . . (IVa), (IVb), (IVc) etc.

Compounds of general formula (I) may be prepared from compounds of formula (II) according to reaction scheme 1. Suitable reaction conditions comprise treating compounds of formula (II) with gaseous hydrogen chloride at low temperature (for example −78 deg C.) followed by treatment with methanolic ammonia.

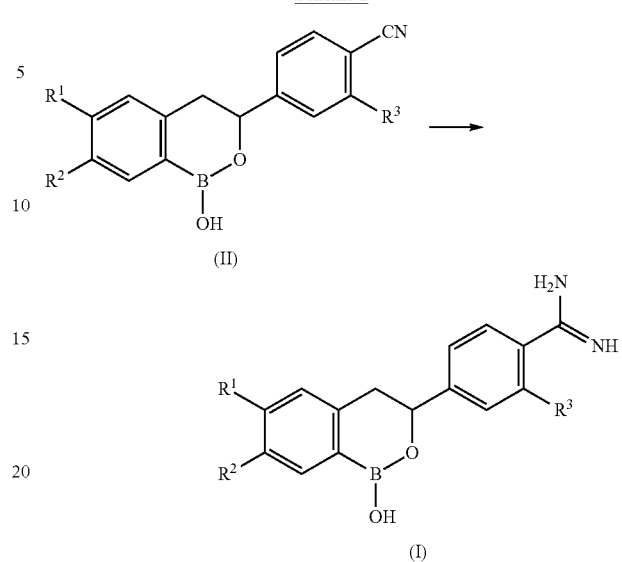

The hydrochloride salt of compounds of formula (I) may be prepared by treating compounds of formula (I) with methanolic hydrochloric acid.

Compounds of general formula (II) may be prepared from compounds of formula (III) according to reaction scheme 2. Suitable reaction conditions comprise mixing compounds of formula (III) with 5,5,5',5'-tetramethyl-2,2'-bi(1,3,2-dioxaborinane), potassium acetate and PdCl$_2$(dppf) in 1,4-dioxane at 130° C.

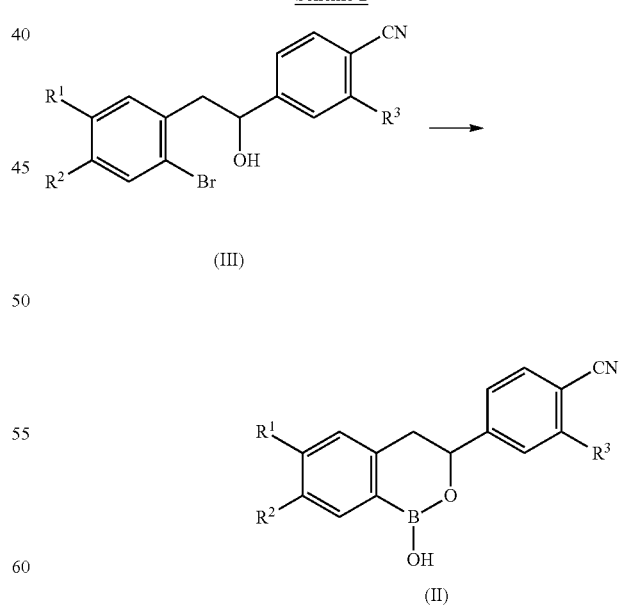

Compounds of general formula (III) may be prepared from compounds of formula (IV) according to reaction scheme 3. Suitable conditions comprise treatment with sodium borohydride in ethanol.

Scheme 3

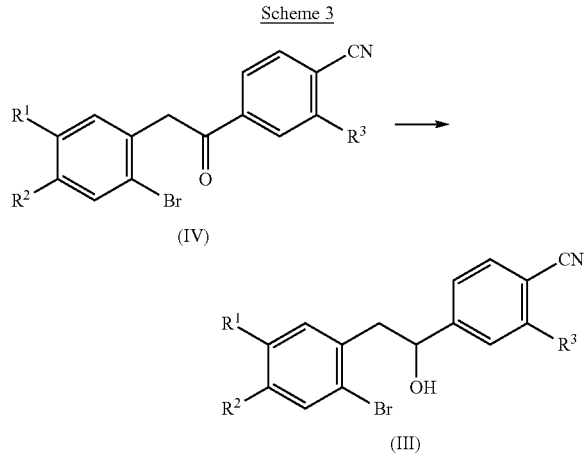

Compounds of formula (IIIa), i.e. compounds of general formula (III) where the carbon atom attached to the hydroxy group is chiral, may be prepared according to the three-step procedure shown in Scheme 4. Treatment with an appropriate asymmetric hydrogenating agent gives an enantiomerically enriched mixture of alcohols (IIIb). Treatment of (IIIb) with chiral acid (V) gives diasteromeric mixture of esters (VI) which may be separated by chromatography or crystallisation. De-esterification reveals the desired chiral alcohol (IIIa).

Scheme 4

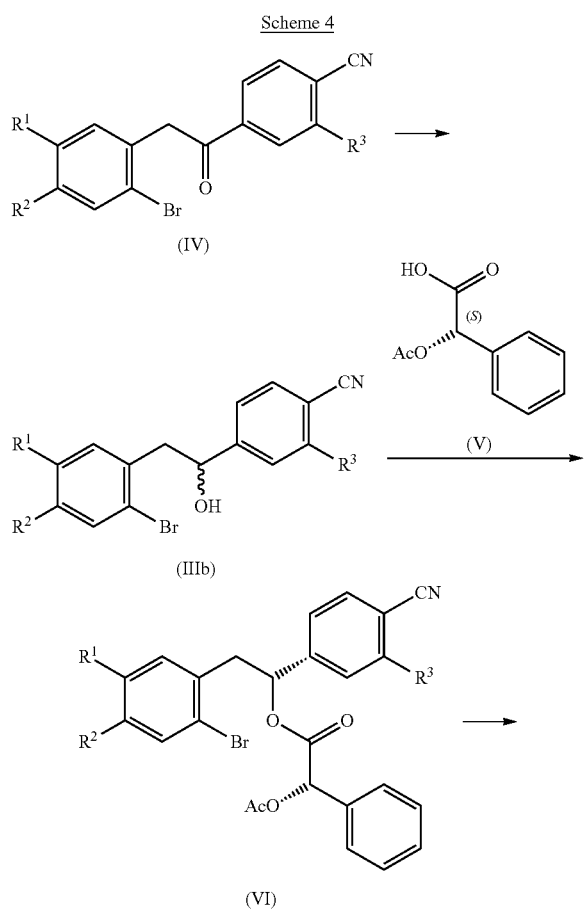

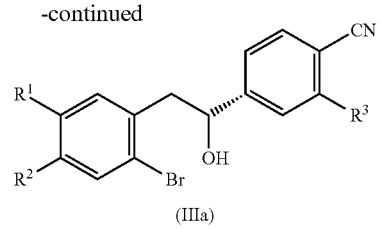

Compounds of formula (IV) may be prepared via a number of methods. For example, Compounds of formula (IV) may be prepared from compounds of formula (VII) and (VIII) according to reaction scheme 5. Suitable reaction conditions comprise heating a solution of (VII), (VIII), xantphos, $Pd_2(dba)_3$ and a base (such as sodium tert-butoxide or cesium carbonate) in dry 1,4-dioxane at elevated temperature.

Scheme 5

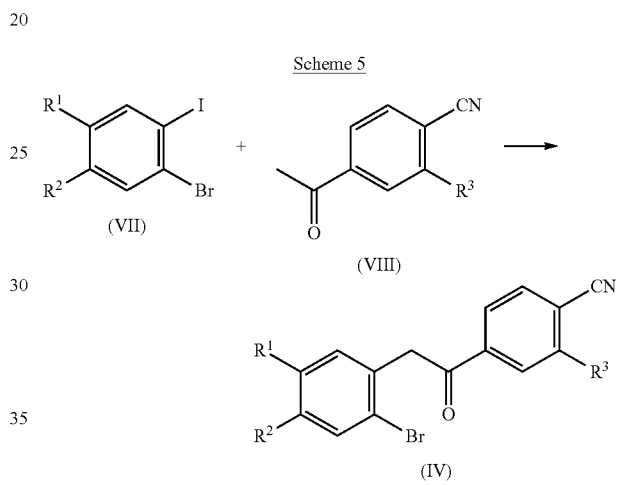

Alternatively compounds of formula (IV) may be prepared from compounds of formula (IX) and (X) according to reaction scheme 6. Suitable conditions comprise treatment with NaHMDS in THF.

Scheme 6

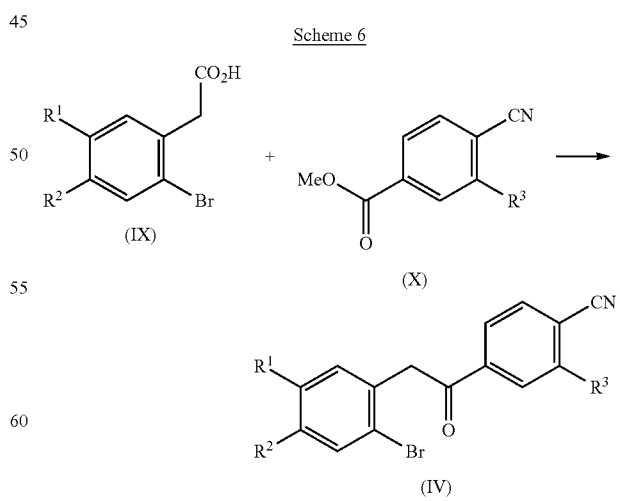

Compounds of formula (Xa), i.e. compounds of general formula (X) where $R^3$ is 3-chlorobenzyloxy or 3-pyridylmethoxy, may be prepared from compounds of formula (XI)

according to reaction scheme 7. Suitable conditions comprise treating 3-chlorobenzyl alcohol or 3-pyridylmethyl alcohol (respectively) with sodium hydride in a suitable solvent (eg., DMF) at low temperature (e.g., 0° C.), followed by dropwise addition of (XI) in a suitable solvent.

form the corresponding acyl chloride, followed by reaction with N,O-dimethylhydroxylamine hydrochloride and trimethylamine.

Scheme 7

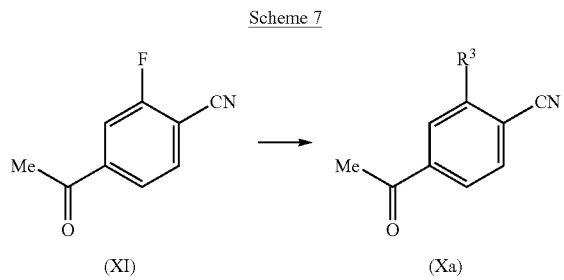

(XI)  (Xa)

Scheme 10

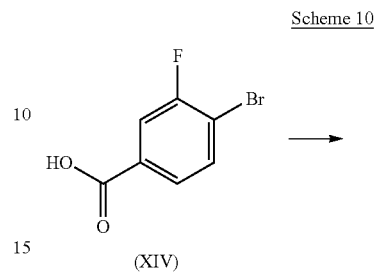

(XIV)

Compound (XI) may be prepared from compounds of formula (XII) according to reaction scheme 8. Suitable reaction conditions comprise reacting (XII), zinc cyanide, tetramethylethylenediamine, $Pd_2(dba)_3$ and xantphos at elevated temperature (e.g., 120° C.)

Scheme 8

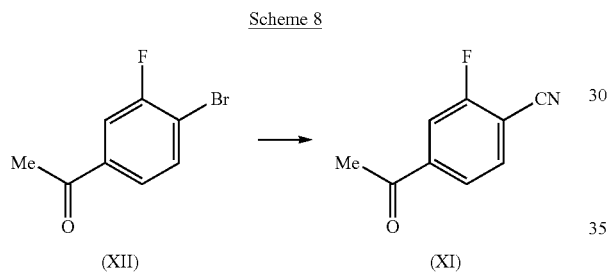

(XII)  (XI)

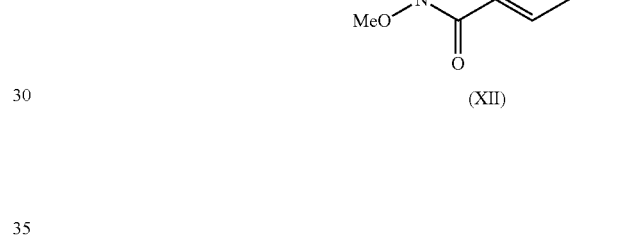

(XII)

Compound (XIV) is known in the art and is commercially available.

Alternatively compounds of formula (Xa) may be prepared from compound (XV) according to reaction scheme 11. Suitable conditions comprise reacting (XV) with 3-chlorobenzyl alcohol or 3-pyridylmethyl alcohol in the presence of triphenylphosphine and (E)-bis(2-methoxyethyl)diazene-1,2-dicarboxylate or through alkylation conditions comprising for example reaction of (XV) with 3-chlorobenzylbromide or 3-pyridylmethylbromide in presence of a base such as potassium carbonate.

Compound (XII) may be prepared from compound (XIII) according to reaction scheme 9. Suitable reaction conditions comprise reacting (XIII) in a suitable solvent (e.g., THF) with methyl magnesium chloride at 0° C.

Scheme 9

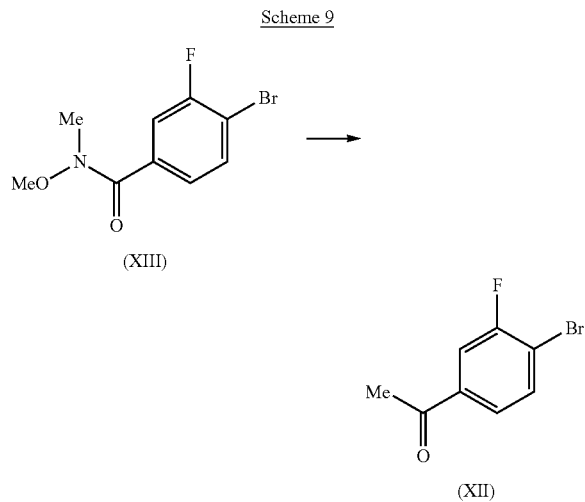

(XIII)

(XII)

Scheme 11

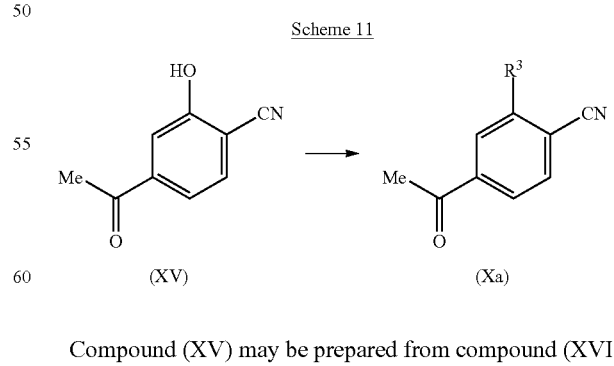

(XV)  (Xa)

Compound (XV) may be prepared from compound (XVI) according to reaction scheme 12. Suitable reaction conditions comprise treating (XVI) with potassium ferrocyanide trihydrate, sodium carbonate and palladium (II) acetate in dimethylacetamide at elevated temperature (e.g., 140° C.).

Compound (XIII) may be prepared from compound (XIV) according to reaction scheme 10. Suitable reaction conditions comprise reacting (XIV) with oxalyl chloride/DMF to Scheme 12

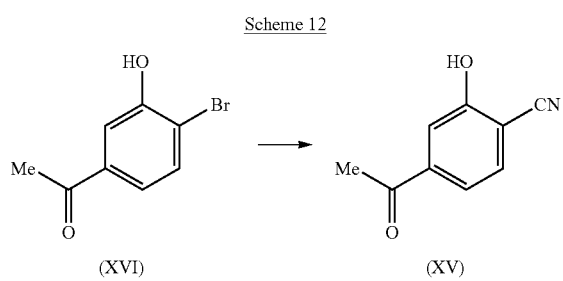

(XVI)    (XV)

Compound (XVI) is known in the art and is commercially available.

The compounds of the invention may be useful in treating diseases or conditions mediated by the KLK-5 pathway.

As used herein, "treat", "treating" or "treatment" in reference to a disease or condition means: (1) to ameliorate the disease or condition or one or more of the biological manifestations of the disease or condition, (2) to interfere with (a) one or more points in the biological cascade that leads to or is responsible for the disease or condition or (b) one or more of the biological manifestations of the disease or condition, (3) to alleviate one or more of the symptoms or effects associated with the disease or condition, (4) to slow the progression of the disease or condition or one or more of the biological manifestations of the disease or condition, and/or (5) to diminish the likelihood of severity of a disease or condition or biological manifestations of the disease or condition.

The compounds of the invention will normally, but not necessarily, be formulated into pharmaceutical compositions prior to administration to a patient by an appropriate route. Accordingly, in another aspect, the invention provides pharmaceutical compositions comprising a compound of the invention and one or more pharmaceutically-acceptable excipients.

As used herein, "pharmaceutically-acceptable excipient" means any pharmaceutically acceptable material present in the pharmaceutical composition or dosage form other than the compound or compounds of the invention. Typically, the material gives form, consistency and performance to the pharmaceutical composition.

The pharmaceutical compositions of the invention typically contain one compound of the invention. However, in certain embodiments, the pharmaceutical compositions of the invention contain more than one compound of the invention. In addition, the pharmaceutical compositions of the invention may comprise one or more additional pharmaceutically active compounds.

Such pharmaceutical compositions of the invention may be prepared and packaged in bulk form wherein a safe and effective amount of a compound of the invention can be dispensed and then given to the patient such as with powders or syrups. Alternatively, the pharmaceutical compositions of the invention may be prepared and packaged as dosage forms wherein each physically discrete dosage form contains a safe and effective amount of a compound of the invention. Accordingly, in another aspect, the invention provides dosage forms comprising pharmaceutical compositions of the invention. Each discrete dosage form typically contains from 0.1 mg to 3000 mg of a compound of the invention.

The compositions of the invention will typically be formulated into dosage forms which are adapted for administration to the patient by the desired route of administration.

For example, dosage forms include those adapted for (1) oral administration such as tablets, capsules, caplets, pills, lozenges, powders, syrups, elixirs, suspensions, solutions, emulsions, sachets and cachets; (2) parenteral administration such as sterile solutions, suspensions, implants and powders for reconstitution; (3) transdermal administration such as transdermal patches; (4) rectal and vaginal administration such as suppositories, pessaries and foams; (5) inhalation and intranasal such as dry powders, aerosols, suspensions and solutions (sprays and drops); (6) topical administration such as creams, ointments, lotions, solutions, pastes, sprays, foams and gels; (7) buccal and sublingual administration such as lozenges, patches, sprays, drops, chewing gums and tablets.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound or compounds of the invention once administered to the patient from one organ, or portion of the body, to another organ, or portion of the body. Certain pharmaceutically-acceptable excipients may be chosen for their ability to enhance patient compliance. Certain pharmaceutically-acceptable excipients may be chosen for their ability to facilitate the release of the compound of the invention at the appropriate rate to treat the condition.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavouring agents, flavour masking agents, colouring agents, anticaking agents, humectants, chelating agents, plasticizers, viscosity increasing agents, rate modifying agents, antioxidants, preservatives, stabilizers, surfactants and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to determine suitable pharmaceutically-acceptable excipients in appropriate amounts for use with the compounds of the invention. In addition, there are a number of resources that are available to the skilled artisan which describe pharmaceutically-acceptable excipients and may be useful in selecting suitable pharmaceutically-acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press). The pharmaceutical compositions of the invention may be prepared using techniques and methods known to those skilled in the art. Some of the methods commonly used in the art are described in Remington's Pharmaceutical Sciences (Mack Publishing Company).

In an embodiment, the dosage form is adapted for topical administration, such as creams, ointments, lotions, solutions, pastes, sprays, foams and gels.

Formulations suitable for topical administration include liquid or semi-liquid preparations suitable for penetration through the skin to the site of inflammation such as liniments, lotions, creams, ointments and pastes suitable for administration to the skin.

Lotions according to the present invention include those suitable for application to the skin. Lotions or liniments for application to the skin may include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as siliceous silicas, and other ingredients such as lanolin, may also be included.

For topical administration, the compound of the invention may comprise from 0.001% to 10% w/w, for instance from 1% to 2% by weight of the formulation. It may however comprise as much as 10% w/w but preferably will comprise less than 5% w/w, more preferably from 0.1% to 3% w/w of the formulation.

It will be appreciated that the invention includes the following further aspects. The diseases and conditions described above extend, where appropriate, to these further aspects. In addition, the embodiments defined above in relation to the first aspect extend to these further aspects.

i) The use of a compound of the invention in the manufacture of a medicament for treating a disease or condition mediated by the KLK-5 pathway. In an embodiment, the disease or condition is selected from the group consisting of: Netherton syndrome, rosacea, atopic dermatitis, psoriasis and itch.

ii) A method of treating a disease or condition mediated by the KLK-5 receptor in a human comprising administering an effective amount of a compound of the invention. In an embodiment, the disease or condition is selected from the group consisting of: Netherton syndrome, rosacea, atopic dermatitis, psoriasis and itch.

iii) A pharmaceutical composition comprising a) a compound of the invention and b) one or more pharmaceutically acceptable excipients.

iv) A pharmaceutical composition comprising a) 0.05 to 3000 mg of a compound of the invention and b) 0.1 to 100 g of one or more pharmaceutically acceptable excipients.

v) A pharmaceutical composition for the treatment of a disease or condition mediated by the KLK-5 pathway. In an embodiment, the disease or condition is selected from the group consisting of: Netherton syndrome, rosacea, atopic dermatitis, psoriasis and itch.

vi) A compound of the invention for use in therapy.

vii) A compound of the invention for use in the treatment of a disease or condition mediated by the KLK-5 pathway. In an embodiment, the disease or condition is selected from the group consisting of: Netherton syndrome, rosacea, atopic dermatitis, psoriasis and itch.

Supporting Compounds

Compounds of the invention and intermediates have been named using either a) ACD/Name PRO 6.02 chemical naming software (Advanced Chemistry Development Inc., Toronto, Ontario, M5H2L3, Canada); or b) MarvinSketch.NET.5.11.4 (ChemAxon Kft. Záhony u. 7, Building HX 1031 Budapest, Hungary)

ABBREVIATIONS

ACN—acetonitrile
CHAPS—cholamidopropyl)dimethylammonio]-1-propanesulfonate)
DMAP—N,N-dimethylpyridin-4-amine
DMF—N,N-dimethylformamide
DMSO—dimethylsulphoxide
DMAP—4-dimethylaminopyridine
EDC—1-ethyl-3-(3-dimethylaminopropyl)carbodiimide
ES—electrospray
GCMS—gas chromatography mass spectrometry
HPLC—High Pressure Liquid Chromatography
IPA—isopropyl alcohol
LCMS—liquid chromatography mass spectrometry
MS—mass spectrometry
rt—retention time
SFC—supercritical fluid chromatography
TFA—trifluoroacetic acid
THF—tetrahydrofuran
UPLC—Ultra Performance Liquid Chromatography LCMS Methods Method 1:

Analytical HPLC was conducted on a X-Select CSH C18 XP column (2.5 μm 30×4.6 mm id) eluting with 0.1% formic acid in water (solvent A) and 0.1% formic acid in acetonitrile (solvent B), using the following elution gradient 0-3 minutes: 5% to 100% B, 3-4 minutes 100% B, at a flow rate of 1.8 ml/minute at 40° C. The mass spectra (MS) were recorded on a Waters ZQ mass spectrometer (scan 200-900 uma) using electrospray positive ionisation [ES+ to give MH+ molecular ions] or electrospray negative ionisation [ES− to give (M-H)− molecular ions] modes with a 20V cone voltage.

Method 2:

Analytical HPLC was conducted on a X-Select CSH C18 XP column (2.5 μm 30×4.6 mm id) eluting with 0.1% formic acid in water (solvent A) and 0.1% formic acid in acetonitrile (solvent B), using the following elution gradient 0-6 minutes: 5% to 100% B, 6-7 minutes 100% B, at a flow rate of 1.8 ml/minute at 40° C. The mass spectra (MS) were recorded on a Waters ZQ mass spectrometer (scan 200-900 uma) using electrospray positive ionisation [ES+ to give MH+ molecular ions] or electrospray negative ionisation [ES− to give (M-H)− molecular ions] modes with a 20V cone voltage.

| Method | Description |
|---|---|
| A | Column: Acquity BEH C18 (50 mm X 2.1 mm, 1.7 μm)<br>Mobile Phase: A: 0.05% Formic acid in water; B: 0.05% Formic acid in ACN<br>Time (min)/% B; 0/3, 0.4/3, 3.2/98, 3.8/98, 4.2/3, 4.5/3<br>Column Temp: 35° C.<br>Flow Rate: 0.6 mL/min |
| B | Column: Acquity BEH C18 (50 mm X 2.1 mm, 1.7 μm)<br>Mobile Phase: A: 0.1% Formic acid in water; B: 0.1% Formic acid in ACN<br>Time (min)/% B: 0/3, 0.4/3, 3.2/98, 3.8/98, 4.2/3, 4.5/3<br>Column Temp: 35° C.<br>Flow Rate: 0.6 mL/min |
| D | Column: XBridge C18 (50 mm × 4.6 mm, 2.5 μm)<br>Mobile Phase: A: 5 mM Ammonium Bicarbonate in water (pH 10). B: 100% ACN<br>Gradient: Time (min)/1% B: 0/5, 0.5/5, 1.5/15, 7/98, 9/98, 9,5/5, 10/5<br>Column Temp: 35° C., Flow Rate: 1.3 ml/min |
| I | Column: Acquity BEH C18 (50 mm × 2.1 mm, 1.7 um)<br>Mobile Phase: A: 5 mM Ammonium Bicarbonate in water (pH-10); B: ACN<br>Time (min)/% B: 0/3, 0.4/3, 7.5/98, 9,5/98, 9.6/3, 10/3<br>Column Temp: 35° C., Flow Rate: 0.6 ml/min |
| J | Column: Acquity BEH C18 (50 mm × 2.1 mm, 1.7 μm)<br>Mobile Phase: A: 0.1% Formic Acid in water; B: 0.1% Formic Acid in ACN<br>Time (min)/% B: 0/3, 0,4/3, 4/98, 4.5/98, 5/3, 5.5/3<br>Column Temp: 35° C., Flow Rate: 0,45 mL/min |
| K | Column: Acquity BEH C18 (50 mm × 2.1 mm, 1.7 μm)<br>Mobile Phase: A: 0.1% Formic Acid in water; B: 0.1% Formic Acid in ACN<br>Time (min)/% B: 0/3, 0.4/3, 2.0/98, 3.4/98, 3.5/3, 4.0/3<br>Column Temp: 35° C., Flow Rate: 0.6 mL/min |
| L | Column: Acquity BEH C18 (50 mm × 2.1 mm, 17 um)<br>Mobile Phase: A: 5 mM Ammonium Bicarbonate in water (pH-10); B: ACN<br>Time (min)/% B: 0/3, 0.4/3, 2.5/98, 3.4/98, 3.5/3, 4.0/3<br>Column Temp: 35° C., Flow Rate: 0.6 ml/min |
| M | Column: Acquity BEH C18 (100 mm X 2.1 mm, 1.7 μm)<br>Mobile Phase: A: 0.05% TFA in water; B: ACN<br>Time (min)/% B: 0/3, 0.4/3, 7.5/98, 9.5/98, 9.6/3, 10/3<br>Column Temp: 35° C.; Flow Rate: 0.45 mL/min |
| N | Column: Acquity BEH C18 (100 mm X 2.1 mm, 1.7 μm)<br>Mobile Phase: A: 0.05% TFA in water; B: ACN<br>Time (min)/% B: 0/3, 0.4/3, 3.5/98, 4.5/98, 5.0/3, 5.5/3.<br>Column Temp: 35° C.; Flow Rate: 0.45 mL/min |
| O | Column: Acquity BEH C18 (50 mm × 2.1 mm, 1.7 um)<br>Mobile Phase: A: 0.05% Formic Acid in Water;<br>B: 0,05% Formic Acid in ACN<br>Gradient Time (min)/% A: 0/97, 0.4/97, 4.0/2, 4.5/2, 5/97, 5.5/97<br>Column Temp: 35° C., Flow Rate: 0.45 ml/min |

GCMS Methods

| Method | Description |
|---|---|
| A | Column: ZB-5MS (30 mm X 0.32 mm, 1 μm)<br>He = 2.0 mL/min; Inj = 230° C.;<br>Program: 100° C./1 min; 20 *C./min/310° C./5.5 min. |

UPLC/HPLC Methods

| Method | Description |
|---|---|
| C | Column: Acquity BEH C18 (100 mm X 2.1 mm, 1.7 μm)<br>Mobile Phase: A 0.1% TFA in water, B: 0.1% TFA in ACN<br>Time (min)/% B: 0/3, 8.5/100, 9.0/100, 9.5/3, 10/3.<br>Column Temp: 50° C.; Flow Rate: 0.55 mL/min |

Chiral HPLC/SFC Methods

| Method | Description |
|---|---|
| A | Column: CHIRALPAK AD-H (250 mm X 4.6 mm, 5 μm)<br>Eluent: A: $CO_2$ = 85%; B: methanol = 15%;<br>Back pressure: 100 bar;<br>Temp: 24.5° C.; Flow Rate: 3 g/min |
| B | Column: CHIRALCEL OD-H (250 mm X 4.6 mm, 5 μm)<br>Eluent: A: $CO_2$ = 75%; B: 30 mM methanolic ammonia in IPA = 25%;<br>Back pressure: 100 bar;<br>Temp: 25° C.; Flow Rate: 3 g/min |
| C | Column: CHIRALCEL OD-H (250 mm X 4.6 mm, 5 μm)<br>Eluent: A: $CO_2$ = 75%; B: 0.5% diethylamine in methanol = 25%;<br>Back pressure: 100 bar;<br>Temp: 24.8° C.; Flow Rate: 3 g/min |
| D | Column: CHIRALCEL, OD-H (250 mm X 4.6 mm, 5 μm)<br>Eluent: A: $CO_2$ = 75%; B: 0.5% isopropyl amine in IPA = 25%;<br>Back pressure: 100 bar;<br>Temp 25° C.; Flow Rate: 3 g/min |

Supporting Compounds/Intermediates

In the procedures that follow, after each starting material, reference to an intermediate is typically provided. This is provided merely for assistance to the skilled chemist. The starting material may not necessarily have been prepared from the batch referred to.

Compound 1

4-(1-Hydroxy-7-(trifluoromethyl)-3,4-dihydro-1H-benzo[c][1,2]oxaborinin-3-yl)-2-(pyridin-3-ylmethoxy)benzimidamide Hydrochloride Salt

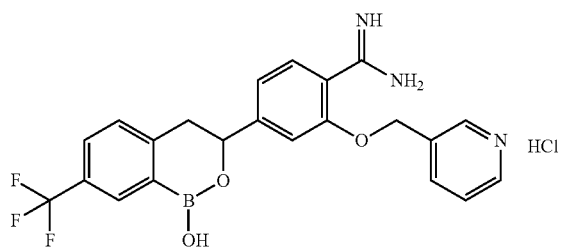 [SMILES: N=C(N)c1ccc(C2Cc3ccc(C(F)(F)F)cc3B(O)O2)cc1OCc1cccnc1 ; Cl]

4-(1-Hydroxy-7-(trifluoromethyl)-3,4-dihydro-1H-benzo[c][1,2]oxaborinin-3-yl)-2-(pyridin-3-ylmethoxy)benzonitrile (Intermediate 1, 150 mg, 0.354 mmol) was dissolved in ethanol (20 mL) in a sealed tube and cooled to −78° C. Hydrogen chloride (g) was slowly bubbled through this solution for 10 min. The reaction was allowed to rise to ambient temperature and to stand overnight at that temperature. The resulting solution was concentrated under reduced pressure using a water bath heated at 30° C. The imidate was dissolved in methanolic ammonia (7N, excess) and stirred overnight in a sealed tube. The reaction was concentrated under reduced pressure and the residue was taken up in water, methanol and ethyl acetate to eliminate the side products. The residual white powder was dissolved in hydrochloric acid (1 M) and concentrated under reduced pressure. The residue was dried at 40° C. and reduced pressure for 3 h to give the title compound (20 mg). $^1$H NMR (D$_6$-DMSO): δH 9.26 (s, 2H), 9.12 (s, 2H), 8.91 (s, 1H), 8.78 (d, J=4.6 Hz, 1H), 8.31 (d, J=7.2 Hz, 1H), 8.08 (s, 1H), 7.80 (d, J=6.6 Hz, 2H), 7.59 (d, J=8.0 Hz, 1H), 7.49 (m, 2H), 7.29 (d, J=8.0 Hz, 1H), 5.41 (m, 3H), 3.27 (m, 1H), 3.18 (m, 1H). LCMS: retention time 1.59 min, MH$^+$ 442 (Method 1).

Intermediate 1

4-(1-Hydroxy-7-(trifluoromethyl)-3,4-dihydro-1H-benzo[c][1,2]oxaborinin-3-yl)-2-(pyridin-3-ylmethoxy)benzonitrile

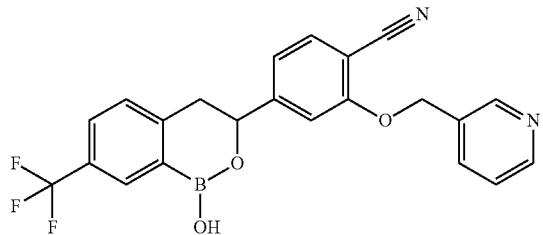 [SMILES: N#Cc1ccc(C2Cc3ccc(C(F)(F)F)cc3B(O)O2)cc1OCc1cccnc1]

4-(2-(2-Bromo-4-(trifluoromethyl)phenyl)-1-hydroxyethyl)-2-(pyridin-3-ylmethoxy)benzonitrile (Intermediate 2, 200 mg, 0.419 mmol) 5,5,5',5'-tetramethyl-2,2'-bi(1,3,2-dioxaborinane) (284 mg, 1.257 mmol) and PdCl2(dppf) (3.68 mg, 5.03 μmol) were mixed in 1,4-dioxane (15 mL) in a sealed tube. This suspension was de-gassed and back-filled with nitrogen. Potassium acetate (82 mg, 0.838 mmol) was added, the reaction vessel was sealed and heated to 130° C. under microwave irradiation for 25 min. The reaction mixture was filtered through a CELITE bed and the filtrate was concentrated in vacuo. The residue was directly loaded onto a 40 g silica column and eluted with 0-30% (ethyl acetate/ethanol 3:1) in cyclohexane. The appropriate fractions were combined and concentrated under reduced pressure. The residue was taken up in acetonitrile and filtered to afford the title compound as a white solid (150 mg). $^1$H NMR (D$_6$-DMSO) includes: δH 9.15 (s, 1H), 8.74 (d, J=1.7 Hz, 1H), 8.60 (dd, J=4.7 Hz, J=1.5 Hz, 1H), 8.06 (s, 1H), 7.93 (dt, J=7.8 Hz, J=1.9 Hz×2, 1H), 7.80 (m, 2H), 7.56 (m, 1H), 7.48 (m, 2H), 7.26 (d, J=8.0 Hz, 1H), 5.38 (m, 3H), 3.25 (m, 1H). LCMS: retention time 2.46 min, MH$^+$ 425 (Method 1).

Intermediate 2

4-(2-(2-Bromo-4-(trifluoromethyl)phenyl)-1-hydroxyethyl)-2-(pyridin-3-ylmethoxy)benzonitrile

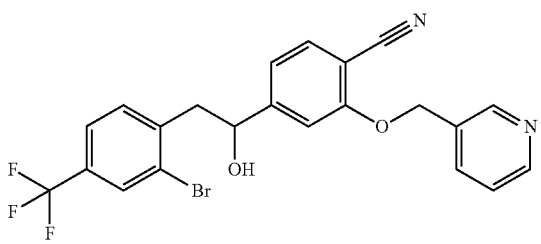 [SMILES: N#Cc1ccc(C(O)Cc2ccc(C(F)(F)F)cc2Br)cc1OCc1cccnc1]

To a solution of 4-(2-(2-bromo-4-(trifluoromethyl)phenyl)acetyl)-2-(pyridin-3-ylmethoxy)benzonitrile (Intermediate 3, 480 mg, 1.010 mmol) in ethanol was added sodium borohydride (38.2 mg, 1.01 mmol) and the reaction was stirred for 1 h at 20° C. The experiment was quenched with hydrochloric acid (1 M). The mixture was stirred for 5 min at ambient temperature, then sodium hydroxide solution (1 M) was added until the pH reached 8. The resulting solution was extracted with ethyl acetate, the organic phase dried over sodium sulphate and filtered. The filtrate was concentrated in vacuo. The residue was loaded onto a 40 g silica column and eluted with a gradient of 0-30% (ethyl acetate/ethanol 3:1) in cyclohexane. The appropriate fractions were combined and concentrated in vacuo to give the title compound as a cream solid (200 mg). $^1$H NMR (D$_6$-DMSO): δH 8.72 (d, J=1.7 Hz, 1H), 8.59 (dd, J=4.8 Hz. J=1.6 Hz, 1H), 7.98 (s, 1H), 7.91 (dt, J=7.9 Hz, J=1.9 Hz×2, 1H), 7.71 (m, 2H), 7.53 (d, J=8.0 Hz, 1H), 7.48 (dd, J=7.9 Hz, J=4.8 Hz, 1H), 7.33 (s, 1H), 7.08 (d, J=8.0 Hz, 1H), 5.77 (d, J=5.1 Hz, 1H), 5.35 (d, J=11.8 Hz, 1H), 5.28 (d, J=12.0 Hz, 1H), 3.08 (m, 2H). LCMS: retention time 2.55 min, MH$^+$ 477/479 (Method 1).

Intermediate 3

4-(2-(2-Bromo-4-(trifluoromethyl)phenyl)acetyl)-2-(pyridin-3-ylmethoxy)benzonitrile

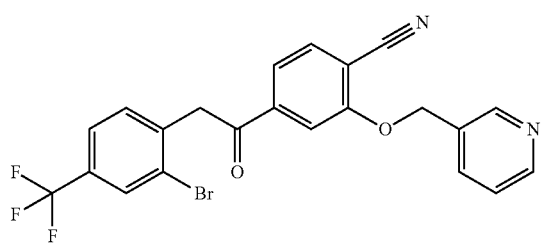 [SMILES: N#Cc1ccc(C(=O)Cc2ccc(C(F)(F)F)cc2Br)cc1OCc1cccnc1]

The reaction was performed in two sealed tubes of equal charge (450 mg of 4-acetyl-2-(pyridin-3-ylmethoxy)benzonitrile in each). A solution of 2-bromo-1-iodo-4-(trifluoromethyl)benzene (1391 mg, 3.57 mmol), 4-acetyl-2-(pyridin-3-ylmethoxy)benzonitrile (Intermediate 4, 900 mg, 3.57 mmol), xantphos (74.3 mg, 0.128 mmol), Pd2(dba)3 (49.0 mg, 0.054 mmol) and sodium tert-butoxide (1029 mg, 10.70 mmol) in dry 1,4-dioxane (8 ml) was heated at 80° C. in a Biotage Initiator microwave for 60 min. The reaction was filtered and the filtrate was concentrated under reduced pressure. The residue was dissolved in ethyl acetate and washed with water. The organic phase was dried over sodium sulphate and filtered. The filtrate was concentrated in vacuo. The residue was loaded onto an 80 g silica column and eluted with a gradient of 0-20% (ethyl acetate/ethanol 3:1) in cyclohexane. The appropriate fractions were combined and concentrated in vacuo to give the title compound as a cream solid (510 mg). $^1$H NMR (D$_6$-DMSO): δH 8.75 (s, 1H), 8.60 (d, J=3.8 Hz, 1H), 8.03 (m, 2H), 7.94 (m, 2H), 7.86 (d, J=8.0 Hz, 1H), 7.80 (d, J=7.6 Hz, 1H), 7.66 (d, J=7.8 Hz, 1H), 7.49 (dd, J=7.6 Hz, J=4.9 Hz, 1H), 5.49 (s, 2H), 4.80 (s, 2H). LCMS: retention time 2.71 min, MH$^+$ 475/477 (Method 1).

Intermediate 4

4-Acetyl-2-(pyridin-3-ylmethoxy)benzonitrile

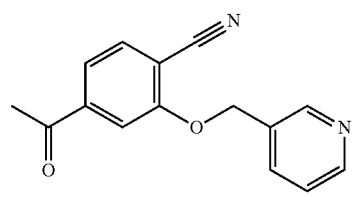 [SMILES: CC(=O)c1ccc(C#N)c(OCc2cccnc2)c1]

4-Acetyl-2-hydroxybenzonitrile (Intermediate 5, 1000 mg, 6.21 mmol) was added to pyridin-3-ylmethanol (745 mg, 6.83 mmol), triphenylphosphine (2441 mg, 9.31 mmol) and (E)-bis(2-methoxyethyl)diazene-1,2-dicarboxylate (2180 mg, 9.31 mmol). The reaction was stirred at 20° C. for 3 days. The reaction mixture was concentrated in vacuo, the residue was dissolved in ethyl acetate and washed with sodium hydroxide solution (1N) and water. The organic phase was dried over sodium sulphate and filtered. The filtrate was concentrated in vacuo and the residue loaded onto an 80 g silica column and eluted with a gradient of 0-20% (ethyl acetate/ethanol 3:1) in cyclohexane. The appropriate fractions were combined and concentrated in vacuo to give the title compound as a white solid (900 mg). $^1$H NMR (D$_6$-DMSO): δH 8.74 (s, 1H), 8.60 (d, J=3.4 Hz, 1H), 7.95 (m, 2H), 7.79 (s, 1H), 7.70 (d, J=8.0 Hz, 1H), 7.49 (dd, J=7.7 Hz, J=4.8 Hz, 1H), 5.45 (s, 2H), 2.66 (s, 3H). LCMS: retention time 1.48 min, MH$^+$ 253 (Method 1).

Intermediate 5

4-Acetyl-2-hydroxybenzonitrile

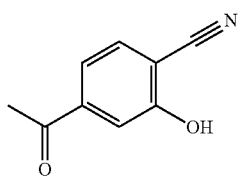

Under inert conditions, potassium ferrocyanide trihydrate (1.179 g, 2.79 mmol) and sodium carbonate (1.971 g, 18.60 mmol) were ground to a fine powder and dried under vacuum at 60° C. for 3 h. A flask was charged with 1-(4-bromo-3-hydroxyphenyl)ethanone (2 g, 9.30 mmol), dimethylacetamide (20 mL, 9.30 mmol) and the potassium ferrocyanide/sodium carbonate mixture then evacuated and filled with nitrogen (×2). Palladium(II) acetate (0.104 g, 0.465 mmol) was added and the reaction was heated at 140° C. for 2 h. The reaction mixture was cooled to ambient temperature and diluted with ethyl acetate (20 mL). The resulting slurry was filtered and the filtrate was washed with ethyl acetate. Hydrochloric acid (1 M) was added to the filtrate and the product was extracted with ethyl acetate. The organic layer was dried over sodium sulphate and filtered. The solution was treated with charcoal and filtered through a silica bed to afford a yellow solution. The solvent was evaporated and the residual pale yellow solid (1.1 g) was used in next reaction without further purification. $^1$H NMR (D$_6$-DMSO): δH 11.48 (s, 1H), 7.79 (d, J=8.0 Hz, 1H), 7.50 (m, 2H), 2.58 (s, 3H). LCMS: retention time 1.73 min, MH$^+$ 160 (Method 1).

Compound 2

(R)-4-(1-hydroxy-7-(trifluoromethyl)-3,4-dihydro-1H-benzo[c][1,2]oxaborinin-3-yl)-2-(pyridin-3-ylmethoxy)benzimidamide Hydrochloride Salt

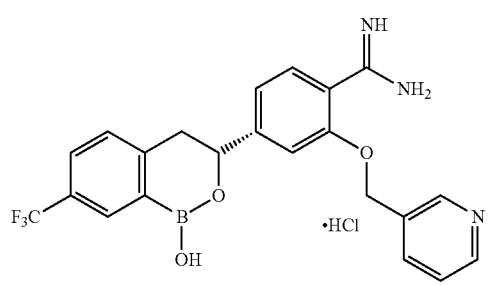

To a stirred suspension of (R)-4-(1-hydroxy-7-(trifluoromethyl)-3,4-dihydro-1H-benzo[c][1,2]oxaborinin-3-yl)-

2-(pyridin-3-ylmethoxy)benzimidamide (Compound 3, 21 g, 47.51 mmol) in methanol (42 mL), was added 4N HCl in methanol (42 mL) at 0° C. under inert atmosphere (a clear solution was observed). After 30 minutes stirring, methanol was evaporated under reduced pressure and the residue was freeze-dried for 9 days. The residue was stirred in acetonitrile (200 mL) for 24 h and the solid isolated by filtration. The solid was dissolved in methanol (50 mL) and diethyl ether (800 mL) added slowly. The solid was isolated by filtration and freeze-drying for 48 h to give the title compound (20.3 g; 99.4% ee) as an off-white solid. $^1$H NMR (400 MHz, DMSO-$d_6$): δ ppm 9.25 (br s, 2H; $D_2O$ exchangeable), 9.16 (br s, 2H; $D_2O$ exchangeable), 8.93 (s, 1H), 8.78 (d, J=5.0 Hz, 1H), 8.36 (d, J=7.9 Hz, 1H), 8.08 (s, 1H), 7.88-7.75 (m, 2H), 7.58 (d, J=7.7 Hz, 1H), 7.52-7.44 (m, 2H), 7.28 (d, J=7.9 Hz, 1H), 5.45-5.34 (m, 3H), 3.33-3.23 (m, 1H), 3.21-3.11 (m, 1H). LCMS (ESI): retention time 2.45 min, MH$^+$ 442; 99.3% (method N). UPLC: retention time 3.56 min, 98.90% (method C). Chiral HPLC: retention time 3.77 min, 99.71% (method C). SOR=+80.42 (c=0.5 in MeOH).

Compound 3

(R)-4-(1-hydroxy-7-(trifluoromethyl)-3,4-dihydro-1H-benzo[c][1,2]oxaborinin-3-yl)-2-(pyridin-3-ylmethoxy)benzimidamide

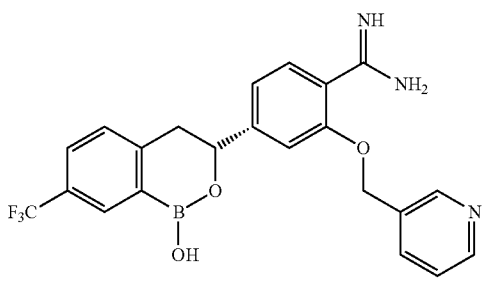

A freshly prepared ammonia solution in methanol (approx. 7 M in solution; 1.5 L) was added to crude methyl (R)-4-(1-hydroxy-7-(trifluoromethyl)-3,4-dihydro-1H-benzo[c][1,2]oxaborinin-3-yl)-2-(pyridin-3-ylmethoxy)benzimidate (Intermediate 6, 50 g) at 0° C. The reaction was allowed to stir at room temperature. After 24 h ammonia solution in methanol (500 mL) was added and stirred at room temperature for 48 h. The solid was isolated by filtration, washed with ammonia solution in methanol (300 mL) and dried under vacuum. The solid was taken in water (1 L) and stirred for 3 h. The solid was filtered off and dried under vacuum to afford the title compound (21 g) as an off-white solid. $^1$H NMR (400 MHz, DMSO-d6; VT-90° C.): δ ppm 8.69 (s, 1H), 8.54-8.53 (d, J=3.5 Hz, 1H), 8.04 (s, 1H), 7.86 (d, J=7.9 Hz, 1H), 7.71 (d, J=7.0 Hz, 1H), 7.51 (d, J=7.9 Hz, 1H), 7.47-7.34 (m, 2H), 7.29 (s, 1H) 7.10 (d, J=7.9 Hz, 1H), 5.30 (dd, J=10.1, 3.7 Hz, 1H), 5.21 (s, 2H), 3.19-3.29 (m, 1H), 3.14-3.09 (m, 1H). LCMS (ESI): retention time 3.60 min; MH$^+$ 442; 95.5% (method M). UPLC: retention time 3.63 min, 97.88% (method C).

Intermediate 6

Methyl (R)-4-(1-hydroxy-7-(trifluoromethyl)-3,4-dihydro-1H-benzo[c][1,2]oxaborinin-3-yl)-2-(pyridin-3-ylmethoxy)benzimidate

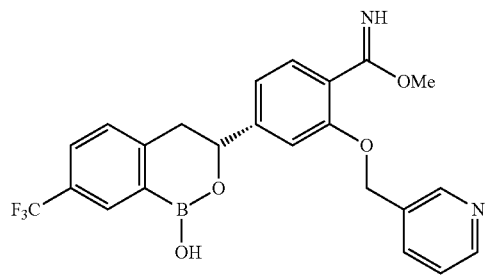

A stirred solution of (R)-4-(1-hydroxy-7-(trifluoromethyl)-3,4-dihydro-1H-benzo[c][1,2]oxaborinin-3-yl)-2-(pyridin-3-ylmethoxy)benzonitrile (Intermediate 7, 40 g, 94.33 mmol) in methanol (1.6 L) was purged with dry HCl gas at −10° C. until complete saturation was observed (dry HC gas was purged for ~9 h). The reaction was allowed to stir at room temperature for 16 h. The reaction solution was concentrated under reduced pressure (below −35° C.) under inert atmosphere conditions to afford the crude title compound (50 g) as a pale yellow sticky solid, which was directly taken for next reaction. LCMS (ESI): retention time 1.46 min; MH$^+$ 457; 78.2% (method K).

Intermediate 7

(R)-4-(1-Hydroxy-7-(trifluoromethyl)-3,4-dihydro-1H-benzo[c][1,2]oxaborinin-3-yl)-2-(pyridin-3-ylmethoxy)benzonitrile

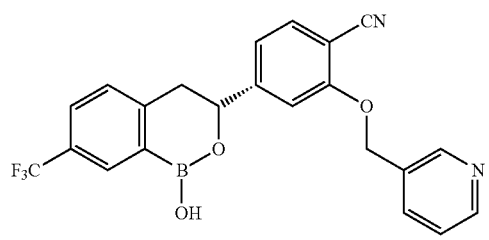

To a stirred and degassed solution of (R)-4-(2-(2-bromo-4-(trifluoromethyl)phenyl)-1-hydroxyethyl)-2-(pyridin-3-ylmethoxy)benzonitrile (Intermediate 8, 125 g, 0.262 mol) and bis(neopentyl glycolato)diboron (2% g, 1.31 mol) in 1,4-dioxane (3.125 L, 25 vol) tert-butyl diphenylphosphine (6.48 g, 26.2 mmol) and Pd(OAc)$_2$ (8.82 g, 13.10 mmol) were added sequentially and the mixture degassed for 10 min. Finally potassium acetate (103 g, 1.048 mol) was added and the mixture degassed for 10 min. The reaction was stirred at 75° C. for 3 h. The reaction mixture was filtered through a CELITE pad with the aid of ethyl acetate (2.5 L). The filtrate was washed with water (5×2 L), brine (2×2 L) dried over Na$_2$SO$_4$, filtered and kept aside for 12 h. The precipitated solid was isolated by filtration and dried under vacuum to afford 85 g of the title compound (96% pure) as an off-white solid.

Pd-scavenger treatment: To a clear solution of (R)-4-(1-hydroxy-7-(trifluoromethyl)-3,4-dihydro-1H-benzo[c][1,2]oxaborinin-3-yl)-2-(pyridin-3-ylmethoxy)benzonitrile (106 g) in 3% methanol in ethyl acetate (3 L) at 65° C., was added Siliamet®-DMT (10.6 g; 0.1 w/w) and stirred for 3 h at same temperature. The resultant hot heterogeneous mixture was filtered through a CELITE pad. The filtrate was concentrated under reduced pressure. The resultant residue was stirred in acetonitrile (1 L) overnight, the solid isolated by filtration and dries to give the title compound (85 g) as an off-white solid.

HNMR (400 MHz, DMSO-$d_6$): δ ppm 9.12 (s, 1H), 8.73 (s, 1H), 8.59 (d, J=4.6 Hz, 1H), 8.06 (s, 1H), 7.92 (d, J=7.9 Hz, 1H), 7.79-7.77 (m, 2H), 7.54 (s, 1H), 7.51-7.44 (m, 2H), 7.26 (d, J=8.1 Hz, 1H), 5.42-5.30 (m, 3H), 3.28-3.22 (m, 1H), 3.17-3.09 (m, 1H). LCMS (ESI): retention time 1.87 min; MH$^+$ 425; 99.63% (method K). UPLC: 99.15% retention time 4.48 min (method C). Chiral HPLC: 99.99% retention 4.28 min (method B).

Intermediate 8

(R)-4-(2-(2-Bromo-4-(trifluoromethyl)phenyl)-1-hydroxyethyl)-2-(pyridin-3-ylmethoxy)benzonitrile

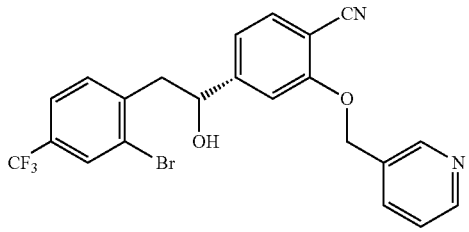

To a stirred solution of (R)-2-(2-bromo-4-(trifluoromethyl)phenyl)-1-(4-cyano-3-(pyridin-3-ylmethoxy)phenyl) ethyl (S)-2-acetoxy-2-phenylacetate (Intermediate 9, 230 g, 352.2 mmol) in methanol (2.3 L) was added potassium carbonate (24.3 g, 176 mmol) and the reaction mixture stirred at 35° C. for 30 min. The reaction solvent was evaporated under reduced pressure. The residue was dissolved in ethyl acetate (2.5 L), washed with water (2 L), brine (2 L), dried over sodium sulphate and concentrated under reduced pressure. The residue was triturated with n-pentane (500 mL) for 1 h, the solid isolated by filtration and dried under vacuum to afford the title compound (155 g, 92% yield: 99.35% ee) as a pale yellow solid. $^1$HNMR (400 MHz, DMSO-$d_6$): δ ppm 8.71 (d, J=1.8 Hz, 1H), 8.58 (dd, J=4.7, 1.4 Hz, 1H), 7.95 (s, 1H), 7.91-7.89 (m, 1H), 7.74-7.65 (m, 2H), 7.52 (d, J=7.9 Hz, 1H), 7.48-7.46 (m, 1H), 7.32 (s, 1H), 7.08 (d, J=7.9 Hz, 1H), 5.75 (br s, 1H), 5.37-5.25 (m, 2H), 4.93 (br s, 1H), 3.12-3.06 (m, 2H). LCMS (ESI): retention time 2.27 min; MH$^+$ 477; 98.62% (method B). Chiral HPLC: 99.67%, retention time 9.13 min (method A).

Intermediate 9

(R)-2-(2-Bromo-4-(trifluoromethyl)phenyl)-1-(4-cyano-3-(pyridin-3-ylmethoxy)phenyl)ethyl (S)-2-acetoxy-2-phenylacetate

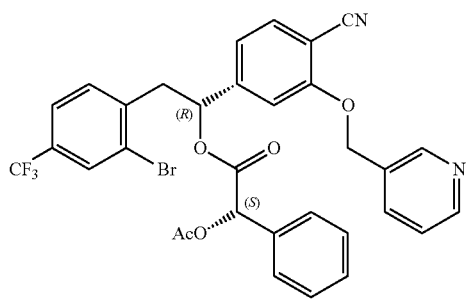

To a stirred solution of (R)-4-(2-(2-bromo-4-(trifluoromethyl)phenyl)-1-hydroxyethyl)-2-(pyridin-3-ylmethoxy)benzonitrile (Intermediate 10, 300 g, 0.628 mol) in THF (3 L), were added (S)-(+)-O-acetyl-mandelic acid (220 g, 1.132 mol), EDC·HCl (264 g, 1.382 mol) and DMAP (23 g, 188.6 mmol) at room temperature and continued stirring for 4 h. The reaction was diluted with ethyl acetate (2 L), washed with water (2×2 L), brine (2 L), dried over anhydrous sodium sulphate and concentrated under reduced pressure. The residue was purified by silica gel column chromatography (silica 100-200 mesh) eluting with 45% ethyl acetate in petroleum ether to afford the diastereomeric mixture (340 g) as a pale yellow solid. HPLC: 61.8% desired diastereomer (retention time 5.85 min, method C) and 18.9% other diastereomer (retention time 5.74 min, method C). The diastereomeric mixture (340 g) in isopropanol (10.2 L, 30 volumes) was heated at 68° C. to get a clear solution. Then the solution was allowed to cool to room temperature, seeded with the desired product (obtained from a previous batch) and left aside for 18 h. The precipitated solid was isolated by filtration, washed with isopropanol (3×300 mL), n-pentane (3×300 mL) and dried under vacuum to afford diastereomerically pure title compound (190 g) as a pale yellow solid. $^1$H NMR (400 MHz, DMSO-$d_6$): δ ppm 8.73 (s, 1H), 8.61-8.60 (m, 1H), 7.92 (d, J=7.9 Hz, 1H), 7.84-7.76 (m, 2H), 7.49 (dd, J=7.7, 4.8 Hz, 1H), 7.44-7.25 (m, 8H), 7.18 (d, J=7.9 Hz, 1H), 6.05-6.03 (m, I1H), 5.94 (s, 1H), 5.42-5.29 (m, 2H), 3.27-3.25 (m, 2H), 2.07 (s, 3H). LCMS (ESI): retention time 2.46 min, MH$^+$ 653; 97% (method L). HPLC: 95.67% retention time 5.87 min (method C).

Intermediate 10

(R)-4-(2-(2-Bromo-4-(trifluoromethyl)phenyl)-1-hydroxyethyl-2-(pyridin-3-ylmethoxy)benzonitrile

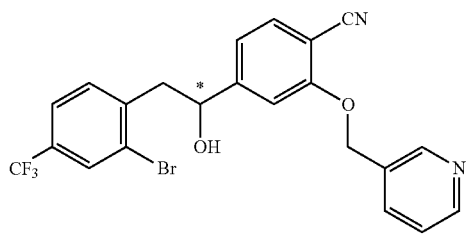 [SMILES: N#Cc1ccc(C(O)Cc2ccc(C(F)(F)F)cc2Br)cc1OCc1cccnc1]

To a stirred solution of 4-(2-(2-bromo-4-(trifluoromethyl)phenyl)acetyl)-2-(pyridin-3-ylmethoxy)benzonitrile (Intermediate 11, 300 g, 0.632 mol) in DMF:iso-propanol:H$_2$O (3 L:3 L:300 mL) mixture, were added potassium formate (266 g, 3.160 mol) and RuCl[(R,R)-Tsdpen]mesitylene (7.08 g, 11.39 mmol) and the reaction stirred for 16 h at room temperature under a nitrogen atmosphere. The iso-propanol was removed under reduced pressure. The resultant reaction mixture was poured into ice cold water. The resulting gummy solid was isolated by filtration, washed with cold water (6×1 L) and dried. The obtained free solid was washed with 10% diethyl ether in pentane (3×400 mL) and dried to afford the title compound (300 g, 99% yield; 69.27% cc) as a yellow solid. $^1$H NMR (400 MHz, DMSO-d$_6$): δ ppm 8.71 (d, J=1.8 Hz, 1H), 8.58 (dd, J=4.7, 1.4 Hz, 1H), 7.95 (s, 1H), 7.91-7.89 (m, 1H), 7.74-7.65 (m, 2H), 7.52 (d, J=7.9 Hz, 1H), 7.48-7.46 (m, 1H), 7.32 (s, 1H), 7.08 (d, J=7.9 Hz, 1H), 5.75 (br s, 1H), 5.37-5.25 (m, 2H), 4.93 (br s, 1H), 3.12-3.06 (m, 2H). LCMS (ESI): retention time 2.21 min; MH$^+$ 477, 93.1% (method B). Chiral HPLC: retention time 16.4 min; 84.54% (method A).

Intermediate 11

4-(2-(2-Bromo-4-(trifluoromethyl)phenyl)acetyl)-2-(pyridin-3-ylmethoxy)benzonitrile

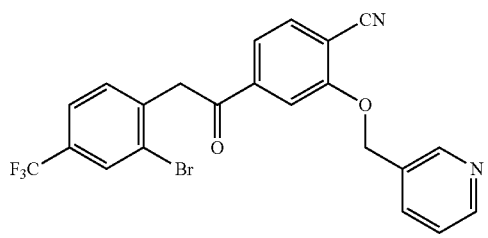 [SMILES: N#Cc1ccc(C(=O)Cc2ccc(C(F)(F)F)cc2Br)cc1OCc1cccnc1]

To a stirred solution of 4-acetyl-2-(pyridin-3-ylmethoxy)benzonitrile (Intermediate 12, 70 g, 278 mmol) and 2-bromo-1-iodo-4-(trifluoromethyl)benzene (116.3 g, 333 mmol) in 1,4-dioxane (1.05 L), cesium carbonate (181 g, 556 mmol) was added and the mixture degassed for 10 min. To this, Xantphos (8.64 g, 16.7 mmol) was added and the mixture degassed for 10 min. Pd$_2$(dba) (7.63 g, 8.33 mmol) were added and the mixture degassed for 10 min. The reaction mixture was heated at 90° C. for 4 h. The reaction mixture was filtered through a CELITE pad and washed with ethyl acetate (200 mL). The filtrate was diluted with water (200 mL), and extracted with ethyl acetate (2×1 L). The organic phase was dried over Na$_2$SO$_4$ and concentrated. The obtained crude product was purified by silica gel column chromatography (silica 100-200 mesh), eluting with 40% ethyl acetate in petroleum ether to afford a yellow solid (55 g). To a stirred solution of 4-acetyl-2-(pyridin-3-ylmethoxy)benzonitrile (Intermediate 12, 350 g, 1.38 mol) and 2-bromo-1-iodo-4-(trifluoromethyl)benzene (581.6 g, 1.66 mol) in 1,4-dioxane (5.25 L), cesium carbonate (905.2 g, 2.77 mol) was added and the mixture degassed for 10 min. To this, Xantphos (43.2 g, 83.3 mmol) was added and the mixture degassed for 10 min. Pd$_2$(dba)$_3$ (38.1 g, 41.6 mmol) were added and the mixture degassed for 10 min. The reaction mixture was heated at 90° C. for 4 h. The reaction mixture was filtered through a CELITE pad and washed with ethyl acetate (3 L). The filtrate was diluted with water (2 L), and extracted with ethyl acetate (2×4 L). The combined organic layer was dried over anhydrous Na$_2$SO$_4$ and concentrated under vacuum. The obtained crude product was purified by silica gel column chromatography (silica 100-200 mesh), eluting with 40% ethyl acetate in petroleum ether to afford a yellow solid (325 g). The solids were combined and washed with diethyl ether (500 mL) to afford the title compound (370 g, 46% combined yield) as a pale yellow solid.

$^1$HNMR (400 MHz, CDCl$_3$): δ ppm 8.71 (d, J=1.8 Hz, 1H), 8.63 (dd. J=4.7, 1.2 Hz, 1H), 7.92-7.83 (m, 2H), 7.78-7.75 (m, 1H), 7.73-7.69 (m, 1H), 7.67 (s, 1H), 7.58 (d, J=7.9 Hz, 1H), 7.40-7.34 (m, 2H), 5.30 (s, 2H), 4.49 (s, 2H); LCMS (ESI): retention time 2.25 min, MH$^+$ 475, 99.1% (method K).

Intermediate 12

4-Acetyl-2-(pyridin-3-ylmethoxy)benzonitrile

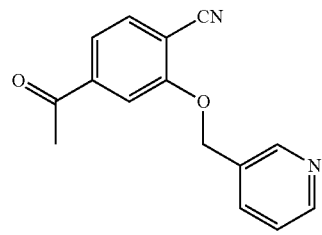 [SMILES: CC(=O)c1ccc(C#N)c(OCc2cccnc2)c1]

To a stirred suspension of sodium hydride (60% in mineral oil; 215 g, 5.36 mol) in DMF (3 L) at 0° C. was added pyridin-3-ylmethanol (627 ml, 6.44 mol) drop-wise over 30 min. The resultant mixture was stirred at room temperature for 30 min. To this mixture, a solution of 4-acetyl-2-fluorobenzonitrile (Intermediate 13, 350 g, 2.15 mol) in DMF (500 mL) was added drop-wise at 0° C. The reaction was then allowed to stir at room temperature for 3 h. Chilled water (7 L) was added. The solid formed was isolated by filtration, washed with diethyl ether (2.5 L) and dried under vacuum to afford the title compound (450 g) as a light brown solid, which was directly taken for next reaction without further purification.

$^1$H NMR (400 MHz, CDCl$_3$): δ ppm 8.71 (s, 1H), 8.63-8.62 (m, 1H), 7.89-7.87 (m, 1H), 7.72 (d, J=7.9 Hz, 1H), 7.64 (s, 1H), 7.61-7.59 (m, 1H), 7.38-7.36 (m, 1H), 5.29 (s, 2H), 2.63 (s, 3H). LCMS (ESI): retention time 1.78 min, MH$^+$ 253, 76% (method J).

Intermediate 13

4-Acetyl-2-fluorobenzonitrile

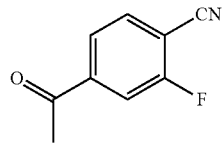

To a stirred solution of 1-(4-bromo-3-fluorophenyl)ethan-1-one (450 g, 2.07 mol) in DMF (3.6 L) in an autoclave, zinc cyanide (607.5 g, 5.18 mol) and then tetramethylethylenediamine (TMEDA, 342 ml, 2.07 mol) were added and the mixture degassed with argon for 10 min. To this, Pd$_2$(dba)$_3$ (56.7 g, 62.1 mmol) and Xantphos (36 g, 62.1 mmol) were added and degassed again with argon for 10 min. The reaction mixture was heated to 120° C. and stirred for 4 h. The reaction was filtered through a CELITE pad. The filtrate was diluted with water (6 L) and extracted with ethyl acetate (2×5 L). The combined organic layers were washed with brine (2 L) and concentrated under reduced pressure to afford the crude product as a brown gum. To a stirred solution of 1-(4-bromo-3-fluorophenyl)ethan-1-one (430 g, 1.98 mol) in DMF (3.44 L) in an autoclave, zinc cyanide (580.6 g, 4.95 mol) and tetramethylethylenediamine (TMEDA, 327 ml, 1.98 mol) were added and the mixture degassed with argon for 10 min. To this, Pd$_2$(dba)$_3$ (54.2 g, 59.4 mmol) and Xantphos (34.4 g, 59.4 mmol) were added and the mixture degassed again with argon. The reaction mixture was heated to 120° C. and stirred for 4 h. The reaction was filtered through a CELITE pad. The filtrate was diluted with chilled water (5 L) and extracted with ethyl acetate (2×3 L). The combined organic layers were washed with brine (1.5 L), dried over sodium sulphate and concentrated under reduced pressure to afford the crude product.

The crude materials from both the batches were combined and purified by silica gel column chromatography (silica 100-200 mesh) eluting with a gradient of ethyl acetate in petroleum ether (25-50% ethyl acetate) to afford the title compound (630 g, 94%) as a yellow solid.

$^1$HNMR (400 MHz, CDCl$_3$): δ ppm 7.84-7.80 (m, 1H), 7.79-7.73 (m, 2H), 2.64 (s, 3H). GCMS: retention time 7.33 min, M$^+$ 163, 92% (method A).

Intermediate 14

1-(4-Bromo-3-fluorophenyl)ethan-1-one

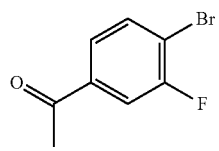

To a stirred solution of 4-bromo-3-fluoro-N-methoxy-N-methylbenzamide (Intermediate 15, 1.17 kg, 4.46 mol) in THF (11.7 L), was added MeMgCl (3 M solution in THF; 2.53 L, 7.59 mol) dropwise at 0° C. The reaction was stirred at room temperature for 2 h. The reaction mixture was quenched by dropwise addition of saturated ammonium chloride solution (200 mL). The resulting solution was diluted with water (6 L) and extracted with ethyl acetate (2×5 L). The combined organic layers were dried over sodium sulphate and concentrated under reduced pressure. The residue was purified by silica gel column chromatography (silica 100-200 mesh), eluting with 8% ethyl acetate in petroleum ether to afford the title compound (890 g, 91.8%) as a pale yellow solid. $^1$HNMR (400 MHz, CDCl$_3$): δ ppm 7.72-7.65 (m, 2H), 7.63-7.59 (m, 1H), 2.59 (s, 3H). GCMS: retention time 7.38 min. M$^+$ 216, 96% (method A).

Intermediate 15

4-Bromo-3-fluoro-N-methoxy-N-methylbenzamide

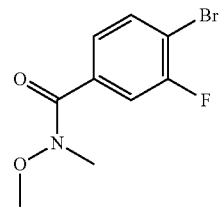

To a stirred solution of 4-bromo-3-fluorobenzoic acid (1.0 kg, 4.566 mol) in dichloromethane (5 L), was added oxalyl chloride (587.2 mL, 6.849 mol) at 0° C., followed by dropwise addition of dry DMF (20 mL, 0.02 vol) at 0° C. Reaction was stirred at room temperature for 3 h. The reaction solvent was evaporated under reduced pressure and argon atmosphere to afford a yellow liquid (1.08 Kg), which was directly taken for next reaction. To a stirred solution of NO-dimethylhydroxylamine hydrochloride (0.532 kg, 5.46 mol) in dichloromethane (10 L) was added triethylamine (2.53 L, 18.19 mol) at 0° C. and the reaction stirred for 15 min. To this mixture, a solution of above prepared liquid (1.08 Kg) in dichloromethane (1 L) was added dropwise. The reaction was stirred at room temperature for 2 h. The reaction mixture was diluted with water (4 L) and extracted with dichloromethane (2×4 L). The combined organic extracts were washed with 1N hydrochloric acid (5 L) then saturated NaHCO$_3$ solution (5 L), dried over anhydrous sodium sulphate and concentrated under reduced pressure to afford the title compound (1.17 kg, 98%) as light brown liquid which was used without further purification. $^1$H NMR (400 MHz, CDCl$_3$): δ ppm 7.61-7.59 (m, 1H), 7.51-7.49 (m, 1H), 7.42-7.40 (m, 1H), 3.55 (s, 3H), 3.36 (s, 3H); LCMS (ESI): retention time 3.29 min, MH$^+$ 262, 93.3% (method 1).

Compound 2 (Alternative Preparation)

(R)-4-(1-Hydroxy-7-(trifluoromethyl)-3,4-dihydro-1H-benzo[c][1,2]oxaborinin-3-yl)-2-(pyridin-3-ylmethoxy)benzimidamide Hydrochloride Salt

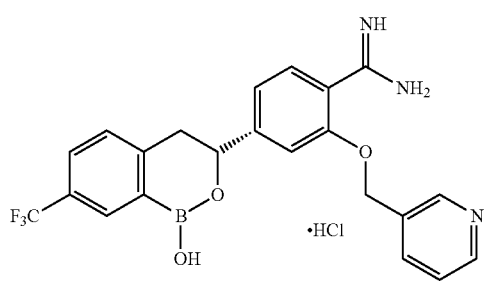

To a stirred solution of (R)-4-(1-hydroxy-7-(trifluoromethyl)-3,4-dihydro-1H-benzo[c][1,2]oxaborinin-3-yl)-2-(pyridin-3-ylmethoxy)benzimidamide (Compound 3, 1.7 g, 3.85 mmol) in methanol (5 mL), was added 3N HCl in methanol (4 mL) at 0° C. and stirred for 20 min. The solvent was evaporated under reduced pressure at 25° C. The residue was dissolved in milliQ ultrapure water (5 ml) and dried by lyophilisation. Due to residual formic acid the salt formation was repeated to give the title compound as an off-white solid (1.745 g, 100%). LCMS (ESI): retention time 1.99 min, MH+ 442; 99.5% (method A). Chiral HPLC: retention time 3.67 min, e.e. 99.85% (method C).

Compound 3 (Alternative Preparation)

(R)-4-(1-Hydroxy-7-(trifluoromethyl)-3,4-dihydro-1H-benzo[c][1,2]oxaborinin-3-yl)-2-(pyridin-3-yl-methoxy)benzimidamide

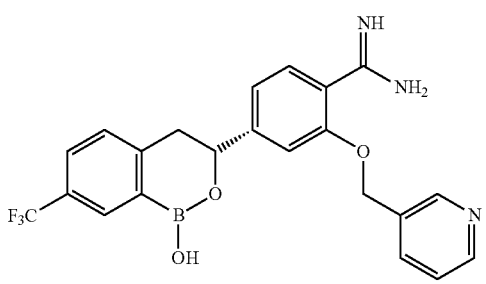

To (R)-4-(1-hydroxy-7-(trifluoromethyl)-3,4-dihydro-1H-benzo[c][1,2]oxaborinin-3-yl)-2-(pyridin-3-ylmethoxy)benzonitrile (Intermediate 6, 2.6 g, 5.70 mmol) was added methanolic ammonia (150 mL) at 0° C. The reaction was allowed to stir at room temperature for 24 h. The reaction solution was concentrated at 25° C. under a nitrogen atmosphere. The residue was purified by preparative HPLC (column: Atlantis T3 C18 (250×19 mm, 5μ, eluent: 0.1% formic acid in water (A)/acetonitrile (B), gradient: 0/10, 10/45, 12.2/45, 13/100, 16/100, 16.5/10, 20/10, flow: 18 ml/min) to give the title compound as a white solid (1.7 g, 63%). LCMS (ESI): retention time 1.99 min; MH+ 442; 99.1% (method O).

Intermediate 6 (Alternative Preparation)

Methyl (R)-4-(1-hydroxy-7-(trifluoromethyl)-3,4-dihydro-1H-benzo[c][1,2]oxaborinin-3-yl)-2-(pyridin-3-ylmethoxy)benzimidate

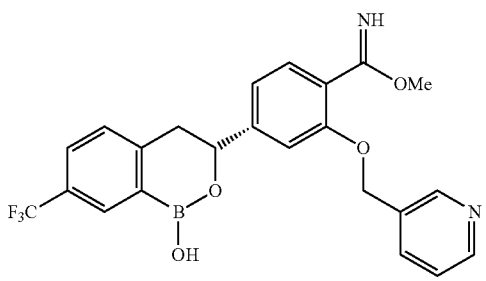

A stirred solution of (R)-4-(1-hydroxy-7-(trifluoromethyl)-3,4-dihydro-1H-benzo[c][1,2]oxaborinin-3-yl)-2-(pyridin-3-ylmethoxy)benzonitrile (Intermediate 7, 2.5 g, 5.89 mmol) in methanol (1.6 L) was saturated with HCl gas at −10° C. The reaction was allowed to stir at room temperature for 24 h. The reaction solution was concentrated under reduced pressure and an argon atmosphere at 25° C. to afford the crude title compound (2.7 g) as a pale yellow sticky solid, which was directly taken for next reaction.

LCMS (ESI): retention time 2.06 min; MH+ 457; 78% (method O).

Intermediate 7 (Alternative Preparation)

(R)-4-(1-Hydroxy-7-(trifluoromethyl)-3,4-dihydro-H-benzo[c][1,2]oxaborinin-3-yl)-2-(pyridin-3-yl-methoxy)benzonitrile

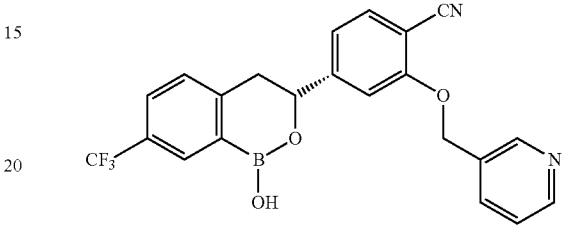

To a stirred solution of 4-(2-(2-bromo-4-(trifluoromethyl)phenyl)-1-hydroxyethyl)-2-(pyridin-3-ylmethoxy)benzonitrile (Intermediate 2, 5 g, 10.47 mmol) in 1,4-dioxane (150 mL), tert-butyl diphenylphosphine (253 mg, 1.04 mmol) was added and the mixture degassed. Pd(OAc)$_2$ (352 mg, 0.52 mmol) was added and the mixture degassed. Bis(neopentyl glycolato)diboron (11.78 g, 52.38 mmol) was added and the mixture degassed. Finally potassium acetate (4.11 g, 41.9 mmol) was added and the mixture degassed. The reaction was stirred at 75° C. in a sealed tube for 2 h. The reaction mixture was filtered through a CELITE pad, treated with charcoal and filtered through CELITE. The filtrate was washed with water (5×2 L), brine (2×50 mL) dried over Na$_2$SO$_4$ and concentrated to afford the racemic compound (5.2 g) as an off-white solid.

This material was combined with a further 8.0 g of crude racemic compound which had been similarly prepared. The combined sample was washed with ether, isolated by filtration and dried (6.13 g).

The 2 enantiomers were separated by chiral SFC (column: CHIRALCEL OD-H 280×4.6 mm, 5μ, solvent CO$_2$ 75%, 30 mm methanolic ammonia 25%, flow: 3.0 g/min, back pressure: 100 bar, temperature: 30° C., uv detection 210 nm). The samples were isolated by distillation under vacuum at 20° C.

Peak 1: (R)-4-(1-hydroxy-7-(trifluoromethyl)-3,4-dihydro-1H-benzo[c][1,2]oxaborinin-3-yl)-2-(pyridin-3-ylmethoxy)benzonitrile, off white solid (2.5 g), LCMS retention time 2.74 min; MH+ 425; 78% (method O); chiral HPLC retention time 4.27 min, 99.9% e.e (method D). Peak 2: (S)-4-(1-hydroxy-7-(trifluoromethyl)-3,4-dihydro-1H-benzo[c][1,2]oxaborinin-3-yl)-2-(pyridin-3-ylmethoxy)benzonitrile off white solid (2.5 g), LCMS retention time 2.73 min; MH+ 425; 78% (method O); chiral HPLC retention time 6.19 min, 98.9% e.e (method D).

Compounds 4 to 8 (see Table) were prepared using general reaction Schemes 1 to 12. Compounds 4 to 8 may also be prepared using procedures (or procedures similar to those) described for the preparation of Compounds 1 to 3 from the corresponding starting materials.

For example, Compound 4 may be prepared in a similar fashion to Compound 3 (Alternative Preparation) from (S)-4-(1-hydroxy-7-(trifluoromethyl)-3,4-dihydro-1H-benzo[c]

[1,2]oxaborinin-3-yl)-2-(pyridin-3-ylmethoxy)benzonitrile [see preparation of Intermediate 7 (Alternative Preparation)].

For example, Compound 5 may be prepared in a similar fashion to Compound 1 by replacing 4-acetyl-2-(pyridin-3-ylmethoxy)benzonitrile with 4-acetyl-2-(3-chlorobenzoxy)benzonitrile in the preparation of Intermediate 3).

For example, Compound 6 may be prepared in a similar fashion to Compound 1 by replacing 4-acetyl-2-(pyridin-3-ylmethoxy)benzonitrile with 4-acetylbenzonitrile in the preparation of Intermediate 3.

For example, Compound 7 may be prepared in a similar fashion to Compound 1 by replacing 2-bromo-1-iodo-4-(trifluromethyl)benzene with 2-bromo-5-chloro-4-fluoro-1-iodobenzene in the preparation of Intermediate 3.

For example, Compound 8 may be prepared in a similar fashion to Compound 1 by replacing 2-bromo-1-iodo-4-(trifluoromethyl)benzene with 2-bromo-1-iodobenzene in the preparation of Intermediate 3.

Any necessary variations in the reaction conditions, reaction time and work-up procedure will be familiar to the skilled chemist. The compounds in the Table were isolated as racemic mixtures of enantiomers except where indicated.

TABLE

| Compound Number | Structure | Mass/ Mass ion | Retention time (min) | LCMS method |
|---|---|---|---|---|
| 4 | (S enantiomer) | 442/ MH$^+$ | 1.62 | A |
| 5 | 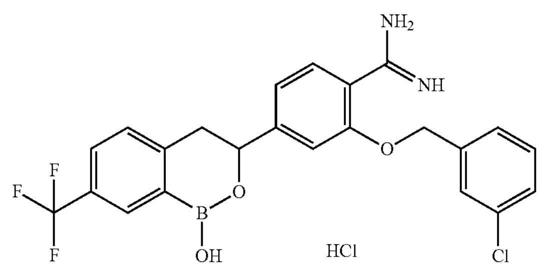 [SMILES: N=C(N)c1ccc(C2Cc3ccc(C(F)(F)F)cc3B(O)O2)cc1OCc1cccc(Cl)c1 ; Cl] | 475/ MH$^+$ | 3.02 | 2 |
| 6 | 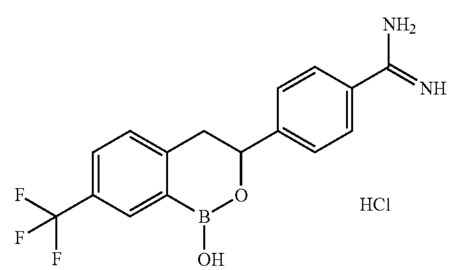 [SMILES: N=C(N)c1ccc(C2Cc3ccc(C(F)(F)F)cc3B(O)O2)cc1 ; Cl] | 335/ MH$^+$ | 1.71 | 1 |
| 7 | 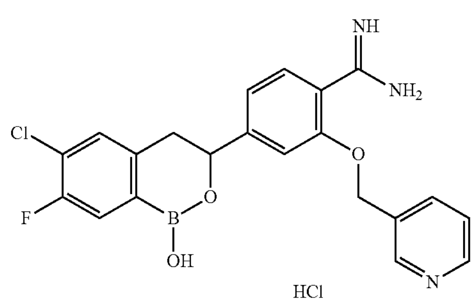 [SMILES: N=C(N)c1ccc(C2Cc3cc(Cl)c(F)cc3B(O)O2)cc1OCc1cccnc1 ; Cl] | 425/ MH$^+$ | 4.10 | D |

TABLE-continued

| Compound Number | Structure | Mass/ Mass ion | Retention time (min) | LCMS method |
|---|---|---|---|---|
| 8 | (structure shown) · HCl | 374/ MH+ | 1.22 | 1 |

Biological Assays

Preparation of KLK5 Protein

Recombinant KLK5 protein was generated from a recombinant baculovirus using the BAC-TO-BAC system (INVITROGEN) (pFastBac_hKLK5_6His-Q-FLAG) expressed in 5 L of *Spodoptera frugiperda* Super 9 insect cells with a viral infection rate of 1.0. The protein was secreted into HYCLONE SFX growth media (GE HEALTHCARE) from which it was extracted on a 5 mL HISTRAP EXCEL column (GE HEALTHCARE). The column was washed with 500 mM NaCl, 20 mM Tris pH 7.4 buffer and the protein eluted using 500 mM imidazole in 250 mM NaCl, 20 mM Tris pH 7.4 buffer. The eluent was captured on a 5 mL, ANTI-FLAG M2 Affinity Gel column (SIGMA). KLK5 was eluted by competing off the bound protein with 0.2 mg/mL FLAG peptide (SIGMA) in 50 mM NaCl, 20 mM Tris-HCl pH 7.4 buffer. 1 M $CaCl_2$ was added to the pooled fractions to a final concentration 2 mM and these were treated with 0.1 U of enterokinase (NOVAGEN) per µg of target protein. The proteins were incubated at room temperature for ~48 h. The cleaved protein was then further purified on a 1 mL Heparin HP HITRAP column (GE HEALTHCARE) in 20 mM MOPS, pH 6.8 buffer, washed with 100 mM NaCl in2 0 mM MOPS, pH 6.8 buffer and eluted with 700 mM NaCl in this buffer. Fractions containing KLK5 were pooled and concentrated using an AMICON concentrator with a molecular weight cut off of 10000 Da. For cryoprotection, glycerol was added to a final concentration of 50%. All purifications were carried out using a semi-automated ÄKTA systems from GE HEALTHCARE.

Kinetic FLINT KLK5 Assay 11 point, 3-fold serial dilutions of each supporting compound were prepared in DMSO and 50 nL of these solutions were dispensed into black LV 384-well plates (GREINER BIO-ONE, Stonehouse, UK) using an ECHO 555 acoustic dispenser (LABCYTE, Sunnyvale, Calif.). This gave a final assay concentration range between 10 µM and 0.5 nM in 5 µL final assay volume. 50 nL DMSO was dispensed into columns 6 and 18 for high and low controls, respectively. The assay plates were sealed and stored at 4° C. until required.

Conditions for the assay of human kallikrein 5 recombinant enzyme (KLK5), were 100 mM sodium phosphate, pH 8, 1 mM CHAPS, 7.5 nM KLK5 enzyme (see above for preparation), 9 uM peptide substrate ((Tos-Gly-Pro-Arg)$_2$ [R110]0.2TFA) in a total reaction volume of 5 µL.

Assays were performed by initially dispensing 2.5 µL of an enzyme solution (15 nM KLK5 in sodium phosphate. pH 8, 1 mM CHAPS) into all wells of the assay plate (except for column 18) then, 2.5 µL of buffer to column 18 (to generate low controls). Reactions were initiated by addition of 2.5 µL of substrate solution [18 uM (Tos-Gly-Pro-Arg)$_2$[R110] 0.2TFA (Cambridge Research Biochemicals) in sodium phosphate, pH 8, 1 mM CHAPS] to all wells. Plates were immediately centrifuged to reach 1000 rpm before transfer to the reader. All additions were made using a MULTIDROP COMBI dispenser (THERMO FISHER SCIENTIFIC). The assay plates were transferred to a PERKIN ELMER VIEWLUX. The plates were excited at 485 nm and the rates of Rhodamine 110 fluorescent emission measured at 535 nm, following cleavage of the substrate by KLK5. Ten measurements were taken over 5 minutes with a read interval of 30 seconds.

Data Analysis

Data analysis was performed within ACTIVITY BASE (ID BUSINESS SOLUTIONS LTD, Surrey, UK).

From the raw data, the enzyme reaction rates were calculated as relative fluorescence units (RFU). Using the 10 reads collected, per well, a straight line was fitted through data. Initial rates were calculated from the slope of the reaction progress curves. The rate data was normalised to % inhibition between high controls in column 6 (0% inhibition) and low controls in column 18 (100% inhibition). Dose response curves were fitted using the IDBS Primary module fit. The data were fitted by means of a four-parameter fit logistic:

$$y = \frac{A-D}{(1+(x/C)^B)} + D$$

Where x is the inhibitor concentration, y is inhibition (%), A is the minimum response, D is the maximum response. C is the IC50 for the curve and B is the Hill slope. The −log (IC50) gives the pIC50.

All Supporting Compounds were tested in the above assay. Each compound was tested more than once. The average pIC50 for each compound is as follows: Compound 1 gave a pIC50 of 8.5.

Compound 2 gave a pIC50 of 8.4.
Compound 3 gave a pIC50 of 7.4.
Compound 4 gave a pIC50 of 8.4.
Compound 5 gave a pIC50 of 8.1.
Compound 6 gave a pIC50 of 8.0.
Compound 7 gave a pIC50 of 8.1.
Compound 8 gave a pIC50 of 8.2.

The invention claimed is:

1. A method of treating a disease or condition mediated by a kallikrein 5 (KLK-5) receptor in a patient comprising at least a step of administering to said patient an effective amount of a compound of formula (I):

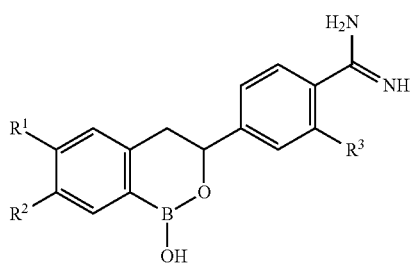

or a pharmaceutically acceptable salt thereof, wherein
$R^1$ is H, $R^2$ is $CF_3$ and $R^3$ is 3-pyridylmethoxy, 3-chlorobenzyloxy or H;
$R^1$ is Cl, $R^2$ is F and $R^3$ is 3-pyridylmethoxy; or
$R^1$ is H, $R^2$ is H and $R^3$ is 3-pyridylmethoxy, wherein the disease or condition is selected from the group consisting of: Netherton syndrome, rosacea, atopic dermatitis, psoriasis and itch.

2. The method according to claim 1 wherein the compound of formula (I) is selected from the group consisting of:

4-(1-hydroxy-7-(trifluoromethyl)-3,4-dihydro-1H-benzo[c][1,2]oxaborinin-3-yl)-2-(pyridin-3-ylmethoxy)benzimidamide;

2-((3-chlorobenzyl)oxy)-4-(1-hydroxy-7-(trifluoromethyl)-3,4-dihydro-1H-benzo[c][1,2]oxaborinin-3-yl)benzimidamide;

4-(1-hydroxy-7-(trifluoromethyl)-3,4-dihydro-1H-benzo[c][1,2]oxaborinin-3-yl)benzimidamide;

4-(6-chloro-7-fluoro-1-hydroxy-3,4-dihydro-1H-benzo[c][1,2]oxaborinin-3-yl)-2-(pyridin-3-ylmethoxy)benzimidamide; and 4-(1-hydroxy-3,4-dihydro-1H-benzo[c][1,2]oxaborinin-3-yl)-2-(pyridin-3-ylmethoxy)benzimidamide.

3. The method according to claim 1 wherein the compound of formula (I) is 4-(1-hydroxy-7-(trifluoromethyl)-3,4-dihydro-1H-benzo[c][1,2]oxaborinin-3-yl)-2-(pyridin-3-ylmethoxy)benzimidamide

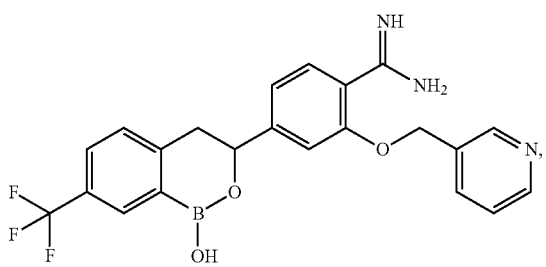 [SMILES: N=C(N)c1ccc(C2Cc3ccc(C(F)(F)F)cc3B(O)O2)cc1OCc1cccnc1]

or a pharmaceutically acceptable salt thereof.

4. The method according to claim 1 wherein the compound of formula (I) is 2-((3-chlorobenzyl)oxy)-4-(1-hydroxy-7-(trifluoromethyl)-3,4-dihydro-1H-benzo[c][1,2]oxaborinin-3-yl)benzimidamide

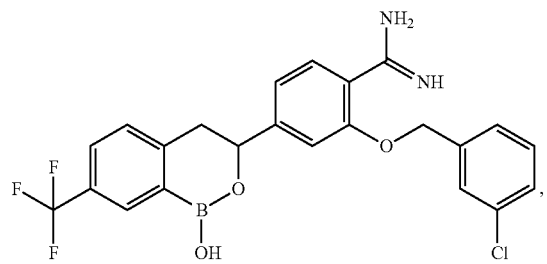 [SMILES: N=C(N)c1ccc(C2Cc3ccc(C(F)(F)F)cc3B(O)O2)cc1OCc1cccc(Cl)c1]

or a pharmaceutically acceptable salt thereof.

5. The method according to claim 1 wherein the compound of formula (I) is 4-(1-hydroxy-7-(trifluoromethyl)-3,4-dihydro-1H-benzo[c][1,2]oxaborinin-3-yl)benzimidamide

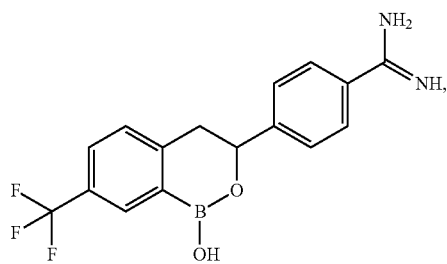 [SMILES: N=C(N)c1ccc(C2Cc3ccc(C(F)(F)F)cc3B(O)O2)cc1]

or a pharmaceutically acceptable salt thereof.

6. The method according to claim 1 wherein the compound of formula (I) is 4-(6-chloro-7-fluoro-1-hydroxy-3,4-dihydro-1H-benzo[c][1,2]oxaborinin-3-yl)-2-(pyridin-3-ylmethoxy)benzimidamide

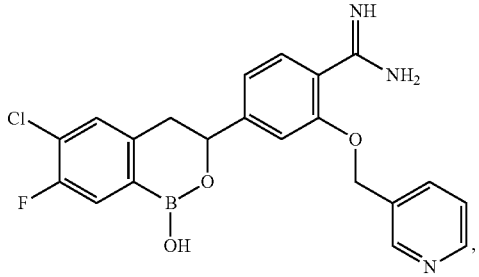 [SMILES: N=C(N)c1ccc(C2Cc3cc(Cl)c(F)cc3B(O)O2)cc1OCc1cccnc1]

or a pharmaceutically acceptable salt thereof.

7. The method according to claim 1 wherein the compound of formula (I) is 4-(1-hydroxy-3,4-dihydro-1H-benzo[c][1,2]oxaborinin-3-yl)-2-(pyridin-3-ylmethoxy)benzimidamide

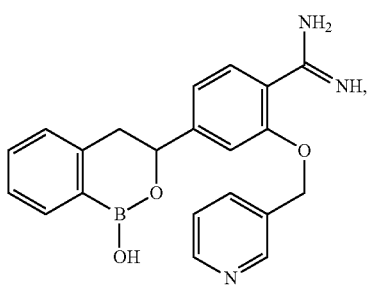 [SMILES: N=C(N)c1ccc(C2Cc3ccccc3B(O)O2)cc1OCc1cccnc1]

or a pharmaceutically acceptable salt thereof.

8. The method according to claim 1 wherein the compound of formula (I) is (R)-4-(1-hydroxy-7-(trifluoromethyl)-3,4-dihydro-1H-benzo[c][1,2]oxaborinin-3-yl)-2-(pyridin-3-ylmethoxy)benzimidamide

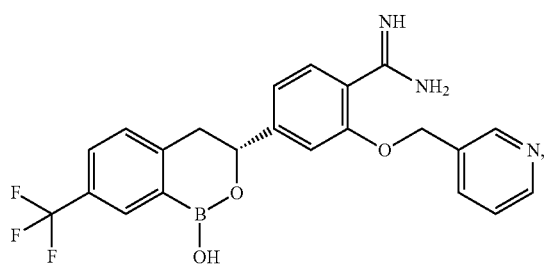 [SMILES: N=C(N)c1ccc([C@H]2Cc3ccc(C(F)(F)F)cc3B(O)O2)cc1OCc1cccnc1]

or a pharmaceutically acceptable salt thereof.

9. The method according to claim 1 wherein the compound of formula (I) is (S)-4-(1-hydroxy-7-(trifluoromethyl)-3,4-dihydro-1H-benzo[c][1,2]oxaborinin-3-yl)-2-(pyridin-3-ylmethoxy)benzimidamide

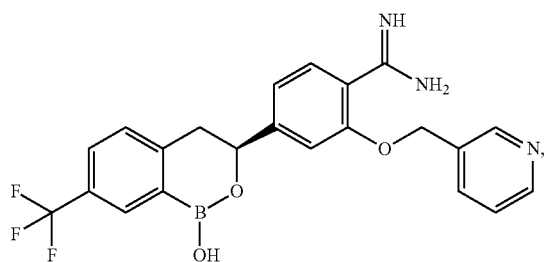 [SMILES: N=C(N)c1ccc([C@@H]2Cc3ccc(C(F)(F)F)cc3B(O)O2)cc1OCc1cccnc1]

or a pharmaceutically acceptable salt thereof.

10. The method according to claim 1 wherein the compound of formula (I) or a pharmaceutically acceptable salt thereof is contained in a pharmaceutical composition with one or more pharmaceutically acceptable excipients.

11. The method according to claim 10 wherein the pharmaceutical composition is formulated in a dosage form adapted for topical administration.

12. The method according to claim 11 wherein the pharmaceutical composition is formulated in a dosage form adapted for topical administration selected from creams, ointments, lotions, solutions, pastes, sprays, foams and gels.

13. The method according to claim 10 wherein the pharmaceutical composition comprises from 0.001% to 10% w/w of the compound of formula (I) or a pharmaceutically acceptable salt thereof.

14. A method for preparing a pharmaceutical composition comprising at least a step of mixing a compound of formula (I):

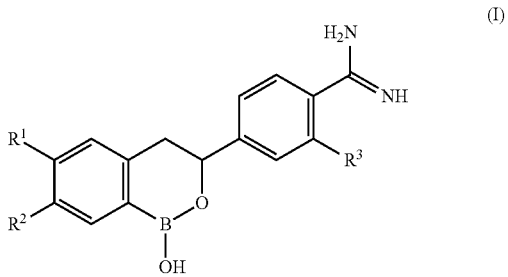

or a pharmaceutically salt thereof, wherein $R^1$ is H, $R^2$ is $CF_3$ and $R^3$ is 3-pyridylmethoxy, 3-chlorobenzyloxy or H;

$R^1$ is Cl, $R^2$ is F and $R^3$ is 3-pyridylmethoxy; or $R^1$ is H, $R^2$ is H and $R^3$ is 3-pyridylmethoxy, with one or more pharmaceutically acceptable excipients.

15. The method of claim 14 comprising at least the step of mixing:
   0.05 to 3000 mg of a compound of formula (I) or a pharmaceutically acceptable salt thereof, with
   0.1 to 100 g of one or more pharmaceutically acceptable excipients.

16. The method of claim 14, wherein the compound of formula (I) is selected from the group consisting of:
   4-(1-hydroxy-7-(trifluoromethyl)-3,4-dihydro-1H-benzo[c][1,2]oxaborinin-3-yl)-2-(pyridin-3-ylmethoxy)benzimidamide;
   2-((3-chlorobenzyl)oxy)-4-(1-hydroxy-7-(trifluoromethyl)-3,4-dihydro-1H-benzo[c][1,2]oxaborinin-3-yl)benzimidamide;
   4-(1-hydroxy-7-(trifluoromethyl)-3,4-dihydro-1H-benzo[c][1,2]oxaborinin-3-yl)benzimidamide;
   4-(6-chloro-7-fluoro-1-hydroxy-3,4-dihydro-1H-benzo[c][1,2]oxaborinin-3-yl)-2-(pyridin-3-ylmethoxy)benzimidamide; and
   4-(1-hydroxy-3,4-dihydro-1H-benzo[c][1,2]oxaborinin-3-yl)-2-(pyridin-3-ylmethoxy)benzimidamide.

17. The method of claim 14, wherein the one or more pharmaceutically acceptable excipients are selected from the group consisting of diluents, fillers, binders, disintegrants, lubricants, glidants, granulating agents, coating agents, wetting agents, solvents, co-solvents, suspending agents, emulsifiers, sweeteners, flavouring agents, flavour masking agents, colouring agents, anticaking agents, humectants, chelating agents, plasticizers, viscosity increasing agents, rate modifying agents, antioxidants, preservatives, stabilizers, surfactants, and buffering agents.

18. The method of claim 14 further comprising the step of formulating the pharmaceutical composition into a dosage form adapted for oral administration; parenteral; transdermal administration; rectal and vaginal administration; inhalation and intranasal; topical administration; or buccal and sublingual administration.

19. The method of claim 18, wherein the dosage form is adapted for topical administration.

* * * * *